(12) United States Patent
Krishnaswamy-Mirle et al.

(10) Patent No.: US 7,179,951 B2
(45) Date of Patent: Feb. 20, 2007

(54) ABSORBENT BARRIER STRUCTURES HAVING A HIGH CONVECTIVE AIR FLOW RATE AND ARTICLES MADE THEREFROM

(75) Inventors: Srinivas Krishnaswamy-Mirle, Liberty Township, OH (US); Mattias Schmidt, Idstein (DE); John Ferney McKibben, West Chester, OH (US); Cornelia Sprengard-Eichel, Frankfurt (DE); Suna Polat, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 440 days.

(21) Appl. No.: 10/265,813

(22) Filed: Oct. 7, 2002

(65) Prior Publication Data

US 2003/0065298 A1    Apr. 3, 2003

Related U.S. Application Data

(63) Continuation-in-part of application No. 09/883,434, filed on Jun. 18, 2001, now abandoned, which is a continuation-in-part of application No. PCT/US00/17084, filed on Jun. 21, 2000.

(51) Int. Cl.
*A61F 13/537* (2006.01)
*A61F 13/514* (2006.01)
*A61F 13/49* (2006.01)

(52) U.S. Cl. ........................ 604/378; 604/367
(58) Field of Classification Search ............ 604/378, 604/367, 381
See application file for complete search history.

(56) References Cited

U.S. PATENT DOCUMENTS

| | | | |
|---|---|---|---|
| 3,837,995 A | 9/1974 | Floden | |
| 3,881,489 A | 5/1975 | Hartwell | |
| 3,916,447 A | 11/1975 | Thompson | |
| 4,338,371 A * | 7/1982 | Dawn et al. | 442/373 |
| 4,636,418 A | 1/1987 | Kennard et al. | |
| 4,648,876 A | 3/1987 | Becker et al. | |
| 4,657,538 A | 4/1987 | Becker et al. | |
| 4,713,068 A * | 12/1987 | Wang et al. | 604/366 |
| 4,798,603 A | 1/1989 | Meyer et al. | |
| 4,828,556 A * | 5/1989 | Braun et al. | 604/365 |
| 5,137,525 A | 8/1992 | Glassman | |
| 5,137,600 A | 8/1992 | Barnes et al. | |
| 5,296,290 A | 3/1994 | Brassington | |
| 5,409,761 A * | 4/1995 | Langley | 428/198 |

(Continued)

FOREIGN PATENT DOCUMENTS

EP    710471 A1 *  5/1996

(Continued)

*Primary Examiner*—Tatyana Zalukaeva
*Assistant Examiner*—Keshia Gibson
(74) *Attorney, Agent, or Firm*—Dara M. Kendall; Matthew P. Fitzpatrick; Ken K. Patel

(57) ABSTRACT

Absorbent articles which provide superior protection against wet through under impact or sustained pressure, and high convective air flow therethrough for skin health and comfort benefits. In particular, an absorbent article comprising an absorbent core and an absorbent barrier structure, wherein the absorbent barrier structure has a hydrohead value of at least about 10 mBars; a convective air permeability of at least about 10 Darcy/mm; and a liquid impact transmission value of less than about 20 g/m$^2$.

6 Claims, 4 Drawing Sheets

U.S. PATENT DOCUMENTS

| | | | |
|---|---|---|---|
| 5,439,458 A * | 8/1995 | Noel et al. | 604/378 |
| 5,482,765 A | 1/1996 | Bradley et al. | |
| 5,558,658 A | 9/1996 | Menard et al. | |
| 5,599,335 A * | 2/1997 | Goldman et al. | 604/368 |
| 5,643,239 A * | 7/1997 | Bodford et al. | 604/370 |
| 5,817,081 A * | 10/1998 | LaVon et al. | 604/378 |
| 5,843,055 A * | 12/1998 | Seger | 604/365 |
| 5,928,209 A | 7/1999 | Bodford et al. | |
| 6,177,607 B1 | 1/2001 | Blaney et al. | |
| 6,316,687 B1 | 11/2001 | Davis et al. | |
| 6,369,292 B1 * | 4/2002 | Strack et al. | 604/370 |
| 6,663,611 B2 * | 12/2003 | Blaney et al. | 604/385.01 |
| 2004/0054344 A1 * | 3/2004 | Roettger et al. | 604/378 |

FOREIGN PATENT DOCUMENTS

| | | |
|---|---|---|
| EP | 0 868 895 A2 | 10/1998 |
| EP | 0 900 571 A2 | 3/1999 |
| WO | WO 95/03114 A1 | 2/1995 |
| WO | WO 96/09165 A1 | 3/1996 |
| WO | WO 97/36561 A1 | 10/1997 |
| WO | WO 97/46750 A1 | 12/1997 |
| WO | WO 98/27920 A1 | 7/1998 |
| WO | WO 98/58609 A1 | 12/1998 |
| WO | WO 99/39672 A1 | 8/1999 |
| WO | WO 99/39673 A1 | 8/1999 |
| WO | WO 99/39674 A1 | 8/1999 |
| WO | WO 00/05065 A1 | 2/2000 |
| WO | WO 00/01499 A1 | 3/2000 |
| WO | WO 00/10497 A1 | 3/2000 |
| WO | WO 00/10498 A1 | 3/2000 |
| WO | WO 00/10500 A1 | 3/2000 |
| WO | WO 00/10501 A1 | 3/2000 |
| WO | WO 01/05346 A1 | 1/2001 |

* cited by examiner

ABSORBENT BARRIER STRUCTURES HAVING A HIGH CONVECTIVE AIR FLOW RATE AND ARTICLES MADE THEREFROM

CROSS REFERENCE TO RELATED APPLICATIONS

This patent application is a continuation-in-part of U.S. patent application Ser. No. 09/883,434, filed Jun. 18, 2001 now abandoned, which is a continuation-in-part of and claims priority under 35 U.S.C. §119 to PCT Application No. US 00/17084, filed Jun. 21, 2000.

FIELD OF INVENTION

The present invention relates to absorbent articles which provide superior protection against wet through under impact or sustained pressure, and high convective air flow therethrough for skin health and comfort benefits. In particular, the present invention relates to an absorbent barrier structure for such articles.

BACKGROUND OF THE INVENTION

Many known absorbent articles such as diapers, incontinence articles, feminine hygiene products, and training pants, typically comprise absorbent core materials located between a liquid pervious body-side liner or topsheet and a vapor permeable, liquid impermeable outer cover or backsheet. The bodyside liner allows bodily liquids to flow through easily and towards the absorbent core. The absorbent core takes up the liquids quickly. Thus, no excessive pooling of liquids occurs on the body-facing surface of the absorbent article. The outer cover is typically liquid impermeable such that there would be no leakage from the absorbent article. However, because the disposable absorbent article may be worn for hours, sometimes after the absorbent article has taken up liquids, perspiration from the wearer's body, and liquid vapors escaped from the absorbent core, can get entrapped in the space between the absorbent article and the wearer's skin, resulting in an increased relative humidity in the occluded area. As is known in the art, the increased relative humidity leads to discomfort and overhydrated skin, which is prone to skin health problems, especially rashes and other contact dermatitis.

Generally, liquid impermeable backsheets are well suited to prevent the leakage of bodily fluids (such as urine, menses or fecal matters) from the absorbent material to the outer garment of a wearer. However, the use of such an impermeable backsheet can result in a high degree of humidity in the absorbent article when the absorbent article is in use such that a relatively elevated skin hydration levels may result.

The problem of high relative humidity near the skin in an absorbent article has been addressed in the art through a number of means. For example, U.S. Pat. No. 5,137,525 uses mechanical means to increase airflow in the article. Alternatively, breathable outer cover having microporous or monolithic films may be used in an absorbent article to allow air and water vapor diffusion. PCT Publications WO 98/58609 discloses absorbent article using other water vapor permeability, liquid impermeable barrier materials as the backsheet. PCT Publication WO 00/10497, WO 00/10498, WO 00/10499, WO 00/10500, WO 00/10501 relate to breathable absorbent articles exhibiting the several properties of the dry and wet articles. The absorbent articles disclosed in these publications typically have high permeability zones within the absorbent core, for, example, by aperturing the absorbent core or by varying high absorbency material content in portions of the core. However, the absorbent articles include microporous backsheets through which the moisture vapor diffuses from the inside to the outside of the absorbent articles. The diffusion mechanism is not very effective in removing moisture vapor. Thus, when the absorbent article is loaded with large amount of liquids, such as urine, the ineffectiveness of the diffusion through a backsheet may result in significantly increased relative humidity between the skin of the wearer and the article.

Another performance parameter of interest for the loaded/ wet absorbent article is its ability to hold the liquid and prevent leakage especially when the article is subjected to pressure or impact force applied by wearer's motion, such as sitting, walking, bending, and falling. The leakage under impact or pressure becomes a serious problem when the absorbent article is loaded with liquids to near its absorbent capacity. Consequently, it is desirable to have an absorbent article which exhibits a balance of properties—on one hand it is desirable to keep the relative humidity in the space between the wearer and the absorbent article (i.e., the "local" environment) in a comfortable range, typically between about 30% to about 70% and more typically between about 30% to about 50% relative humidity. Further, the absorbent article should desirably have the ability to hold liquids without leakage, especially when the article is heavily loaded (i.e., at or near its absorbent capacity). It is also desirable to provide an absorbent article which manages the relative humidity level within the "local" (i.e., the space between the wearer and the absorbent article) environment by a convective transport mechanism. It is further desirable to provide an absorbent article having a carefully designed combination of chassis elements such that the "local" conditions (e.g., relative humidity, skin temperature) are optimized for maintaining or improving skin health.

Typically, to reduce the humidity level within the space between the absorbent article and the wearer's skin, breathable polymer films have been used as the outer cover for the absorbent article. The breathable films are typically constructed with micropores to provide substantial liquid impermeability and some diffusive air/vapor permeability.

Other disposable absorbent articles have been designed to provide breathable regions in the form of breathable panels or perforated openings in the backsheet or in the core to help ventilate the garment. Articles using perforated components or breathable panels often exhibit excessive leakage or wet-through of liquids from the article. Moreover, the wearer's movements (e.g., sitting, falling, walking, lying) may subject the absorbent article to physical forces, such as impact, compression, bending and the like, which may lead to increased leakage and wet-through. The leakage/wet-through problem becomes more severe under higher impact or pressure, heavy discharges and/or extended wear time.

Alternatively, multi-layered backsheets or outer covers have been used to address the wet-through problem. For example, breathable materials such as a fibrous textile or a nonwoven web have been used in the outer cover, either alone or in laminates with the microporous film. The relatively open structures of such materials allow air or vapor to diffuse through easily. The laminates may provide improved liquid impermeability and diffusive air/vapor permeability. The materials may be treated to further improve the liquid impermeability. However, the laminates still do not provide satisfactory protection against wet through under impact and/or sustained pressure. Further, the transport of air or vapor through the laminates via a diffusive mechanism is not as effective as the transport via a convective mechanism.

An alternative approach to the wet-through problem is to improve the absorbent material such that little or no liquid comes into contact with the backsheet, thereby preventing wet-through. This is typically achieved by increasing the amount of absorbent material in the article. However, this approach may lead to an increase in thickness of the article and a decrease in comfort as well as a decrease in vapor/air permeability through the article.

Another approach to the wet-through problem is to place formed films between the core and the backsheet. Formed films having apertures in the shape of slanted cones are disclosed in PCT publications WO 99/39672, WO 99/39673 and WO 99/39674. However, after compaction or sustained pressure, these formed films fail to maintain their formed shape; consequently, they fail to provide the desired balance of properties. The compaction or sustained pressure condition may occur before consumer use (e.g., during packaging, shipping, and storage), or during use (e.g., when the wearer sits or falls on the absorbent article).

Therefore, it is desirable to have absorbent articles that provide consumer comfort, in terms of reduced relative humidity within the absorbent article at a desirable overall thickness, and still achieve satisfactory wet-through protection.

It is also desirable to provide absorbent articles which manage the relative humidity within the space between the article and the wearer's skin to maintain good skin health. Further, it is desirable to manage the relative humidity within the absorbent article by an effective convective transport mechanism, and, optionally some degree of diffusive transport mechanism may be incorporated as well.

Additionally, it is desirable to provide absorbent articles wherein an optimal local i.e., within the space between the article and the wearer's skin) condition for skin health and wearer comfort is achieved by careful designs of components of the article. Specifically, it is desirable to provide an absorbent barrier structure having the desired wet-through protection and air/vapor permeability. Further, the absorbent barrier structure has a desirable thickness for wearer comfort.

It is desirable to provide absorbent articles comprising a barrier absorbent structure that can be exposed to compact and/or sustained pressure conditions for at least 24 hours without substantially degrading its performance, such as air permeability, liquid impermeability and resistance to leakage under impact or sustained pressure.

SUMMARY OF THE INVENTION

The present invention relates absorbent articles with improved protection and comfort by use of an absorbent barrier structure. The absorbent article of the present invention may comprise an absorbent core and an absorbent barrier structure, wherein the absorbent barrier structure may have a hydrohead value of at least about 10 mBars, a convective air permeability of at least about 10 Darcy/mm, and a liquid impact transmission (LIT) value of less than about 20 grams per square meters.

In one embodiment, the absorbent barrier structure may comprise one barrier layer disposed adjacent to the garment-facing surface of the absorbent core, and one reservoir layer disposed adjacent to the garment-facing surface of the barrier layer. In another embodiment, an additional barrier layer may be added to the opposite surface of the reservoir layer. In a further embodiment, the absorbent article may include a dampness management layer.

DETAILED DESCRIPTION OF THE INVENTION

Definitions

Figure 1:
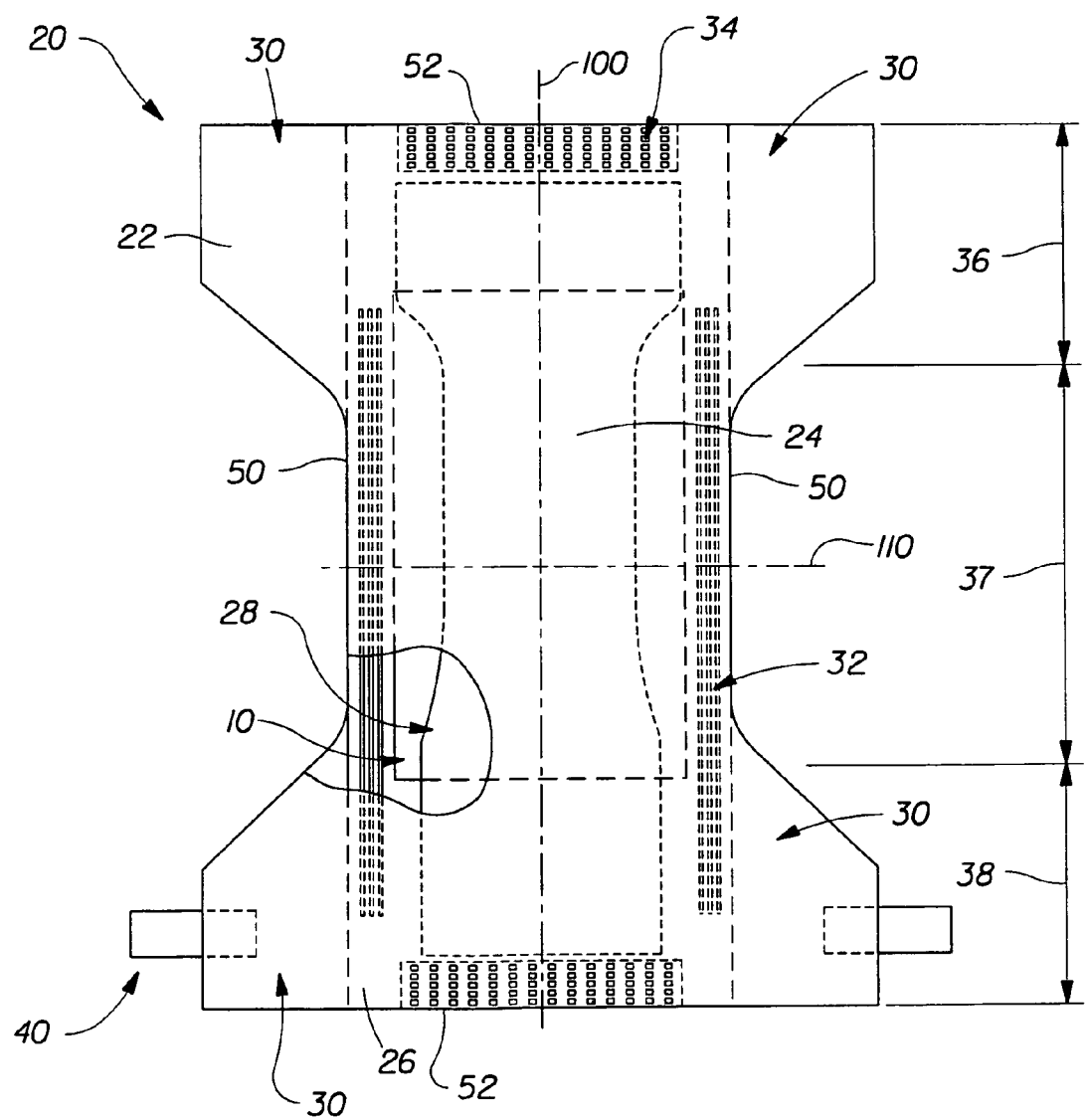
FIG. 1 is partially broken top plan view of an absorbent article containing the absorbent barrier structure of the present invention.

As used herein, the term "absorbent articles" refers to devices which absorb and contain body exudates, and, more specifically, refers to devices which are placed against or in proximity to the body of the wearer to absorb and contain various exudates discharged from the body. Absorbent articles may include diapers, training pants, adult incontinence undergarments, feminine hygiene products, breast pads, and the like. As used herein, the term "body fluids" or "body exudates" includes, but is not limited to, urine, fecal matter, blood, vaginal discharges, and sweat.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "zone" refers to a region or an area comprising a material being physically, chemically, or visually distinguishable from surrounding or adjoining materials. Various zones of materials may include transitional zones between them. The zones may be positioned in the z-dimension or in the xy-dimension. As used herein, the term "xy-dimension" refers to the plane orthogonal to the thickness of a member, core or article when the member, core or article is in a flat-out state. The xy-dimension usually corresponds to the length and width, respectively, of a structure or an article in a flat-out state. As used herein, the term "z-dimension" refers to the dimension orthogonal to the length and width of a structure or an article in a flat-out state. The z-dimension usually corresponds to the thickness of the structure or article.

As used herein, the term "unitary structure" refers to a structure comprising materials having different characteristics joined together to form an integral entity such that the materials are substantially inseparable physically, and the unitary structure exhibits properties resulting from the combination of the materials therein. The materials may be arranged in a face-to-face relationship in the z-dimension, or in a side-by-side and/or overlapping relationship in the xy-dimension.

As used herein, the term "operatively associated" refers to a structure comprising different materials positioned at least in partial contact with each other in use. The materials are physically separable and each exhibits properties that can be measured individually. The materials may be arranged in a face-to-face relationship in the z-dimension, or in a side-by-side and/or overlapping relationship in the xy-dimension.

As used herein, the term "bonded" or "joined" refers to different materials being attached in at least a portion thereof. The attached portion may be random or may have a pattern such as stripes, spirals, dots, and the like. The attached portion may be located at the peripheries, in the surface area (continuously or discontinuously), or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "composite structure" refers to a multi-zoned structure wherein the materials comprising the zones may be operatively associated or bonded. The zones may even be in intimate contact such that the composite has a unitary structure. Further, the zones may be positioned in a layered (face-to-face) arrangement, or a side-by-side and/or overlapping arrangement As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "nonwoven web" refers to a web that has a structure of individual fibers which are interlaid to form a matrix, but not in an identifiable repeating manner. Nonwoven webs may be formed by a variety of processes known to those skilled in the art, for example, meltblowing, spunbonding, wet-laying, air-laying, and various bonding-carding processes.

The present invention relates to absorbent articles with improved protection and comfort by use of an absorbent barrier structure. This is achieved by the selection of individual components meeting specific requirements such that the combination thereof provides the absorbent articles with the desired performance.

A typical absorbent article of the present invention may comprise an air/vapor permeable, liquid impermeable outer cover, a liquid permeable bodyside liner or topsheet, an absorbent core between the outer cover and the bodyside liner, and an absorbent barrier structure positioned between the outer cover and the absorbent core.

The absorbent barrier structure of the present invention balances the properties of convective air flow and absorptive barrier property. The convective air flow property is effective in reducing the relative humidity within the space between the absorbent article and the wearer's skin. The combination of liquid absorption and the liquid barrier property provides protection against the wet-through problem, and is especially beneficial when the absorbent article is under impact and/or sustained pressured conditions.

The absorbent barrier structure is a composite structure having at least one barrier zone and at least one reservoir zone. The barrier zone is resistant to liquid penetration so that the outflow of liquids from the absorbent core is substantially slowed or retarded to allow additional time for the absorbent core to acquire, distribute and retain the liquids to its full absorbent capacity. Suitable materials for the barrier zone should have a hydrohead value of at least about 10 mBars. The reservoir zone absorbs and retains any errant liquid that escapes both the core and the barrier zone, and thus, provides added protection against wet-through. The zones of the absorbent barrier structure provide a combination of properties, which effectively protect against the wet-through problem, even under extreme conditions, such as impact or sustained pressure.

The following detailed description of the absorbent barrier structure of the present invention is in the context of a disposable diaper. However, it is readily apparent that the absorbent barrier structure of the present invention is also suitable for use in other absorbent articles such as feminine hygiene products, training pants, incontinence articles, and the like. It is also apparent that the absorbent barrier structure of the present invention is suitable for use in other hygiene or health care products, such as bandages, dressings, wipes, bibs, surgical drapes, surgical gowns, and the like.

The Barrier Structure or the Absorbent Barrier Structure

The present invention provides a barrier structure which allows convective transport of air or water vapor though this structure. Particularly, the structure of the present invention achieves the desirable convective air flow capacity without sacrificing the barrier protection against wet-through. When the barrier structure is included in an absorbent article, the resulting absorbent article shows effective reduction of the relative humidity in the space between the absorbent article and the wearer. Consequently, the barrier structure reduces incidents of skin irritation and/or rash and improves skin health and wearer comfort.

Convective transport capacity is different from the diffusive transport capacity. The convective transport is driven by a gas or air pressure differential and is typically at a much higher transport rate than the diffusive transport, which is driven by random molecular movements. A typical example of diffusive transport includes the moisture migration through the pores of a microporous films such as those known in the art as the backsheet materials, or through the molecular structure of a nonporous monolithic film such as that made from HYTREL® (available from DuPont, Wilmington, Del.). Convective transport, on the other hand, is directed by the air pressure differential between the inside and the outside of the article. Though the local pressure (i.e., the local pressure within the space between the article and the wearer) and the pressure of the environment (i.e., outside the article) are substantially the same, small changes in the local pressure may lead to convective air/vapor flow towards the outside of the article. Factors that may lead to convective transport include, but are not limited to, movements by the wearer, small pressure and/or temperature differential between the local and the outside environment, and the like.

With the advances made to absorbent articles using elastic materials and elastic components, the absorbent articles now provide a tighter seal (i.e., less gapping) against the wearer's body to minimize fluid leakage to the outside. Consequently, the convective air flow through the gaps is substantially reduced, leading to a humid and hot local environment. While absorbent cores typically have some air permeability; the air permeability typically is reduced when the cores absorb liquid (i.e., become loaded). The loaded cores can be vented (i.e., made air permeable) relatively easily, typically by venting means, such as holes, baffles, and the like. Alternatively, openness of the core structures can be achieved by selected arrangements of permeable materials.

These vented or open-structured cores generally require a leakage protection component, which is typically a microporous film backsheet or a relatively thick nonwoven fabric that provides liquid impermeability and/or leakage protection. However, these liquid impermeable components may reduce the air permeability of the article. In contrast, the barrier structure of the present invention allows the convective air flow through the structure itself without sacrificing leakage protection property.

In some embodiments, the barrier structure of the present invention also provides liquid absorbency and good liquid retention capability. Thus, it is also an absorbent barrier structure. The liquid retention capability is especially beneficial when wearer's motions, such as sitting, falling, lying, bending, walking, may apply pressure/forces on the loaded (i.e., wetted with bodily fluids) absorbent body and/or the adjacent absorbent barrier structure and may lead to leakage or wet-through. Thus, when the absorbent barrier structure is included in an absorbent article, the resulting absorbent article not only provides effective convective air flow capacity, but also provides effective protection against wet-through, even when the article is subjected to pressure or impact forces.

Typically, the absorbent barrier structure is positioned between the absorbent core and the outer cover, preferably adjacent to the garment-facing side of the absorbent core. The absorbent barrier structure is a composite structure, which comprises a plurality of individual zones of materials that are joined or operatively associated together. Alternatively, the plurality of zones may be combined into a unitary structure such that the individual zones become physically inseparable. The individual zones of the absorbent barrier structure may be coextensive or non-coextensive, depending on the requirements of the absorbent article. The individual zones may be joined by attachment means such as those well known in the art.

In some embodiments, a member is directly bonded to the other member by affixing the member directly to the other member. In other embodiments, a member is indirectly secured to the other member by affixing one member to intermediate member(s), which in turn are bonded to the other member. For example, the zones may be bonded together by a uniform continuous layer of adhesive, or an array of separate lines, spirals, or droplets or beads of adhesive. The adhesive may be applied continuously or intermittently. For example, each application of the adhesive spans the length of the absorbent barrier structure and is separated from one another by a selected distance. The adhesive is applied to tack the zones together for handling the webs in the assembly process. Preferably, the adhesive is applied to portions of the surface of the absorbent barrier structure, leaving sufficient open (i.e., free of adhesives) surface areas for air/vapor permeability. Alternatively, the adhesive may be applied to modify the liquid impermeability. Typically, the open or adhesive-free surface area is no less than about 50%, preferably no less than about 70%, more preferably no less than about 80%, and most preferably no less than about 90% of the total surface area of the absorbent barrier structure. Suitable adhesives may be HL-1258 from H.B. Fuller Company of St. Paul, Minn., and H2031 F from Ato-Findley Inc. of Milwaukee, Wis.

In one embodiment, the adhesive may be applied in one or more strips along the peripheries of the zones. In another embodiment, the adhesive may be applied in spaced-apart stripes aligned with the longitudinal centerline of the diaper when it is used in a diaper. In another embodiment, the adhesive may be applied to the web in three stripes along the longitudinal centerline of the diaper. Each stripe is 22 mm wide (in the lateral direction of the diaper) and the two outer stripes are disposed at or near (about 4 mm from) the longitudinal peripheries.

The adhesive is typically applied from its softened or melted state to the surface of at least one of the materials comprising the absorbent barrier structure. Typically, the adhesive is heated to at least above its softening temperature prior to being applied to a substrate surface. Once applied, the adhesive is allowed to cool and harden/solidify. Various methods for softened or melted state application of adhesives are known. Methods particularly suitable for use herein include, but are not limited to, spraying, dipping, gravure printing, and extrusion.

Alternatively, the attachment means may comprise heat bonding, pressure bonding, ultrasonic bonding, mechanical bonding (via, for example, entanglements, cohesive forces, electric or static charges), hydraulic needling or any other suitable attachment means or combinations of these attachment means as are known in the art.

The individual zones may be arranged in layers, wherein individual zones are in an operable, intimate contact with at least a portion of the adjacent layer. Such contacts may be random, or may have a regular pattern, such as dots, stripes, and the like. Preferably, each layer is connected to at least a portion of an adjacent layer of the absorbent barrier structure by a suitable bonding and/or attachment means. In another embodiment, the individual zones may be arranged in an operable, intimate contact along at least a portion of its peripheries with the adjacent layer of the absorbent barrier structure.

The absorbent barrier structure of the present invention may be constructed to have a convective air permeability of at least about 1 Darcy/mm, preferably at least about 10 Darcy/mm, more preferably at least about 30 Darcy/mm, and most preferably at least about 50 Darcy/mm. Convective air permeability is especially effective in removing moisture vapor from inside the absorbent article, resulting in a lower humidity in the local environment next to the skin.

Though the liquids are mainly absorbed by the absorbent core, the absorbent barrier structure provides additional leakage protection against errant liquids that are not absorbed by or are released from the absorbent core. Thus, the absorbent barrier structure of the present invention preferably has at least some liquid absorbency.

Liquid absorbency may vary, depending on the materials used in the absorbent barrier structure, the surface tension of the liquid being tested for absorbency, and the contact angle between the test liquid and the material. An absorbent barrier structure suitable for use herein typically has an absorbency (as measured by Test Method G using a 0.2 wt % Triton® solution) of at least about 1 g/g, typically from about 1 to about 100 g/g, preferably from about 5 to about 50 g/g, more preferably from about 10 to about 30 μg.

Further, the absorbent barrier structure of may also have a liquid retention capability, in order to provide the additional leakage protection, especially under impact and/or sustained pressure conditions. The absorbent barrier structure may have a liquid impact transmission value (as measured by Test Method C) of less than about 20 $g/m^2$, preferably less than about 15 $g/m^2$, more preferably less than about 10 $g/m^2$, and most preferably less than about 6.5 $g/m^2$.

Also related to the leakage protection performance, it is desirable that the absorbent barrier structure has a certain degree of resistance to liquid penetration. Thus, the absorbent barrier structure may have a hydrohead value (as measured by Test Method B) of at least about 10 mBars, preferably at least about 30 mBars, more preferably at least about 50 mBars, and most preferably at least about 75 mBars. In some embodiments, the absorbent barrier structure may have a hydrohead value in the range from about 30 to about 100 mBars.

It is also desirable that the absorbent barrier structure provides leakage protection in terms of a static liquid transmission value (measured according to Test Method D). In this respect, the absorbent barrier structure of the present invention has a static liquid transmission value of less than about 45 g/m$^2$, preferably less than about 30 g/m$^2$, more preferably less than about 20 g/m$^2$, and most preferably less than 13 g/m$^2$, at 15 minutes after impact. Further, the absorbent barrier structure of the present invention has a static liquid transmission value of no more than about 50 g/m$^2$, preferably no more than about 35 g/m$^2$, more preferably no more than about 20 g/m$^2$, at 60 minutes after impact.

In another aspect, after the absorbent barrier structure has been subjected to the compaction condition such as that described below in the Test Method F, it does not suffer substantial changes in barrier properties. The structural integrity during compaction and recovery after compaction are desirable for practical purposes. The absorbent articles are typically compacted into a package for shipping and storage. When the articles are eventually removed from the compaction for the intended use, the material or structure that fails to recover to its pre-compaction state may fail to provide the properties it was originally designed for. Thus, the absorbent barrier structure of the present invention desirably has a post-compaction air permeability decrease of no more than 35%, preferably no more than 25% decrease and most preferably no more than 15% decrease, compared to its pre-compaction air permeability. In a preferred embodiment, the absorbent barrier structure has the post-compaction air permeability as disclosed above, after 7 days, preferably after 30 days, more preferably after 90 days.

The thickness and basis weight of the absorbent barrier structure may vary, depending on the materials used, the properties desired, the intended use, the construction, and the like. For example, thickness and/or basis weight may affect the diffusive breathability and/or the convective air permeability between the interior of an article and the outside, the absorbency and/or leakage protection of the article, the fit of the article to the wearer's body, the wearer's comfort, and like effects that typically relate to thickness of a structure. Typically, the absorbent barrier structure of the present invention intended for use in an absorbent article has a thickness of less than about 1.5 mm, preferably less than about 1.2 mm, and more preferably less than about 1.0 mm. The thickness of the absorbent barrier structure suitable for use in an absorbent article should also have a minimal thickness greater than about 0.1 mm, preferably greater than about 0.2 mm. Further, the absorbent barrier structure of the present invention suitable for use in an absorbent article typically has a basis weight in the range of from about 20 gsm (g/m$^2$) to about 200 gsm (g/m$^2$), preferably from about 30 gsm (g/m$^2$) to about 150 gsm (g/m$^2$), more preferably from about 40 gsm (g/m$^2$) to about 120 gsm (g/m$^2$), and most preferably from about 50 gsm (g/m$^2$) to about 100 gsm (g/m$^2$).

The absorbent barrier structure typically comprises two zones: a barrier zone and a reservoir zone. The barrier zone is "substantially impermeable" to liquids, including water, urine, menses, and other bodily fluids. The term "substantially impermeable" means that the barrier zone exhibits a resistance to liquid penetration but does not necessarily eliminate liquid wet-through. In other words, it is possible for liquid to penetrate and flow through the barrier zone under certain conditions, such as under impact force, under high applied pressure, or under sustained (i.e., continuously applied) pressure for a period of time. The reservoir zone is liquid absorbent. When the reservoir zone is positioned adjacent to the barrier zone, any wet-through and/or leakage from the barrier zone may be absorbed by the reservoir zone. In addition, the reservoir zone may also absorb errant liquids from the absorbent core. Thus, the combination of the barrier zone and the reservoir zone achieves the unique balance of properties that, when exposed to liquids, the barrier zone provides a resistance to liquid wet-through, and the reservoir zone absorbs any errant liquids that break through the resistance of the barrier zone. That is, the absorbent zone provides the added protection against the liquid wet-through problem. When the absorbent barrier structure of the present invention is positioned adjacent to a loaded absorbent core, it provides the additional protection against wet-through, particularly when the liquid loading level is high and/or the loaded absorbent core is under a sudden, high impact force or sustained forces/pressure.

This additional wet-through protection is especially beneficial for absorbent articles used in high liquid loading applications (e.g., diapers, training pants, pull-on diapers, or adult incontinence products). The wet-through protection is also beneficial when the absorbent articles are subjected to sudden impact or sustained pressure (e.g., when babies or adults fall, sit down, roll, sleep).

The absorbent barrier structure of the present invention is also beneficial when the absorbent core is subjected to gushes of liquids. The resistance to liquid wet-through provides by the barrier zone serves to temporarily slow down the gushes of liquids, possibly pooling the liquids at the interface between the absorbent core and the barrier zone. The slowed flow and pooling provide the additional time for the absorbent core to acquire and distribute the liquids to other regions of the core beyond the point of insult. Consequently, the absorbent core may achieve its full absorbent capacity.

Figure 2A:
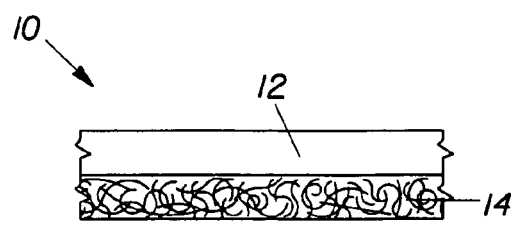
FIG. 2A is a cross sectional view of an absorbent barrier structure of the present invention which has a barrier layer and a reservoir layer.
Figure 2B:
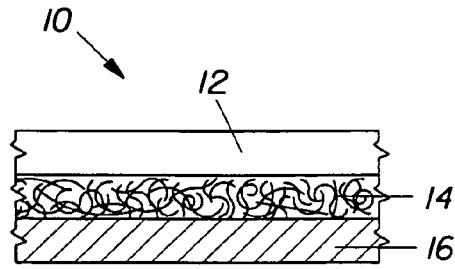
FIG. 2B is a cross sectional view of an absorbent barrier structure of the present invention which has a reservoir layer disposed between two barrier layers.

Exemplary absorbent barrier structure of the present invention are illustrated in the following figures. FIG. 2A is a cross sectional view of an embodiment of the absorbent barrier structure of this invention. The absorbent barrier structure 10 comprises a barrier layer 12 and a reservoir layer 14. In another embodiment, as shown in FIG. 2B, an additional barrier layer 16, may be disposed on the other side of the reservoir layer 14 such that the reservoir layer 14 is sandwiched between the barrier layers 12 and 16. The first and the second barrier layers may be made of identical or different (in terms of construction of the web, basis weight, thickness, porosity, fiber denier, material, and the like) fibrous webs.

Figure 3A:
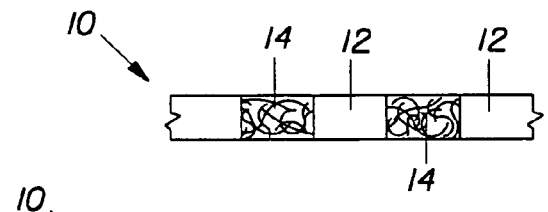
FIGS. 3A–3D are cross sectional views of alternative embodiments of the absorbent barrier structure of FIG. 2A.
Figure 3B:
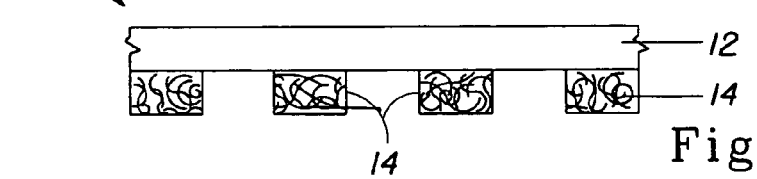
Figure 3C:
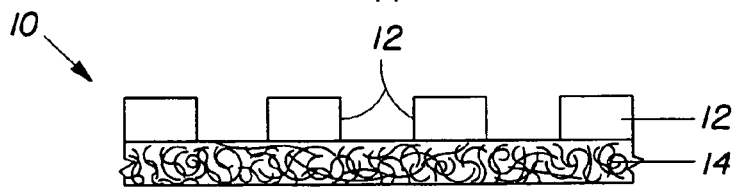
Figure 3D:
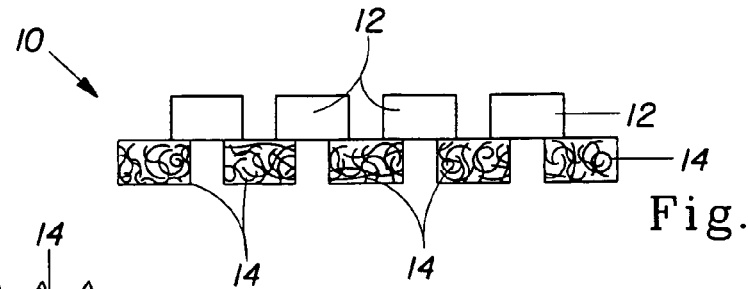
Figure 4A:
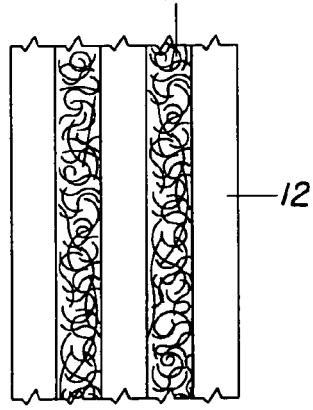
FIG. 4A is a top plan view of the absorbent barrier structure of the present invention which has a barrier zone and a reservoir zone in a side-by-side arrangement.
Figure 4B:
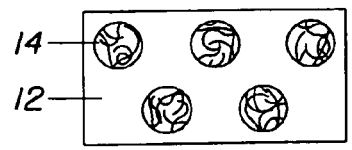
FIG. 4B is a top plan view of the absorbent barrier structure of the present invention in an alternative arrangement.

Various arrangements of the barrier zone and the reservoir zone are shown in FIGS. 3A–3D. In FIG. 3A, multiple barrier zones 12 and reservoir zones 14 are arranged in a side-by-side relation, wherein the barrier zones 12 and the reservoir zones 14 are preferably stripes. In FIG. 3B, the barrier zone 12 is a continuous web and the reservoir zone 14 is disposed adjacent thereto in a discontinuous pattern, such as stripes, circles, ellipses, squares, and the like. In FIG. 3C, the reservoir zone 14 is a continuous web and the barrier zone 12 is disposed adjacent thereto in a discontinuous pattern, such as stripes, circles, ellipses, squares and the like. In FIG. 3D, the discontinuous barrier zones 12 overlap at least partially with the discontinuous reservoir zones 14, and each may have the shape of stripes, circles, ellipses, squares, and the like.

In all of the embodiments illustrated in FIGS. 2A–3D, at least a portion of the barrier zone is positioned adjacent to the garment-facing side of the absorbent core. In one embodiment, the absorbent barrier structure may be substantially coextensive with the absorbent core. Alternatively, the absorbent barrier structure may be stripes or patches that extend only to portions of the absorbent core. In another embodiment, the absorbent barrier structure may extend beyond the outer edges of the absorbent core or only through the length and width of the central portion of the absorbent core. In one embodiment, the barrier zone and the reservoir zone are arranged in a layered relation, wherein the barrier layer is disposed immediately adjacent to the garment-facing side of the absorbent core. Configurations in which the barrier zone has at least the same length and width of the absorbent core are desirable. Furthermore, the reservoir zone need not have the same dimensions as the barrier zone.

The Reservoir Zone

The reservoir zone desirably absorbs, spreads and retains liquids such as urine, blood and other body exudates. The reservoir zone has a garment-facing surface, a body-facing surface, front and rear edges, and side edges. The reservoir zone absorbs and retains the errant liquids that escape from other components such as the absorbent core and the barrier zone. Thus, the reservoir zone provides additional protection against wet-through.

The thickness and basis weight of the reservoir zone may vary, depending on the materials used, the properties desired, the intended use, the openness of the construction, and the like. Specifically, the thickness of the reservoir zone may affect the air/gas permeability, the absorbency and/or leakage protection of the barrier absorbent structure, as well as the comfort and fit of the absorbent article, and like effects typically related to the thickness of a structure. Thus, the reservoir zone typically has a thickness of less than about 1.5 mm, preferably less than about 1.0 mm, and more preferably less than about 0.8 mm. The reservoir zone may desirably have a minimal thickness to provide for adequate absorbency and structural integrity. The minimal thickness of the reservoir zone is typically no less than about 0.2 mm, preferably no less than about 0.1 mm, more preferably no less than 0.05 mm, and most preferably no less than 0.02 mm. Further, the basis weight of the reservoir zone is typically in the range from about 5 gsm (g/m$^2$) to about 120 gsm (g/m$^2$), preferably from abut 10 gsm (g/m$^2$) to about 100 gsm (g/m$^2$), and more preferably from about 30 gsm (g/m$^2$) to about 80 gsm (g/m$^2$).

When compared to the absorbent core, the reservoir zone absorbs fluids more readily (i.e., a faster fluid uptake) and releases fluids more readily. The reservoir zone typically has an absorbency of at least about 1 g/g, preferably at least about 5 g/g, more preferably at least about 10 g/g, based on Test Method G and using 0.2 wt % TRITON® as the test fluid. The absorbency of the reservoir zone is preferably less than about 30 g/g, and more preferably less than about 20 g/g. Further, the reservoir should have an absorbency that is less than that of the absorbent core by at least about 20%, preferably by about 30%.

The reservoir zone may desirably have an open structure such that its air or gas permeability is at least equal to that of the resulting absorbent barrier structure. The convective air/vapor permeability of the reservoir zone is typically at least about 1 Darcy/mm, preferably at least about 10 Darcy/mm, more preferably at least about 30 Darcy/mm, and most preferably at least about 50 Darcy/mm.

Further, the openness of the structure may enhance absorbency by holding or absorbing the fluids in the interstitial spaces in the open structure. Suitable open structures may include fibrous webs (e.g., woven or nonwoven webs); absorbent foams (e.g., porous or reticulated foams); fibrous wads; and the like.

In one embodiment, the reservoir zone is made of fibrous webs. The fibrous webs constituting the reservoir zone need not necessarily comprise absorbent fibers, so long as the webs are absorbent. Thus, the constituent fibers may simply be hydrophilic fibers and have no absorptive capacity by themselves.

In one embodiment, the reservoir zone is made of primarily cellulosic fibers which are primarily hydrogen bonded to one another. Cellulosic fibers may be natural or processed, and may be chemically stiffened, modified or cross-linked. Processed cellulosic fibers may include commercially available fibers made of regenerated cellulose or derivatized cellulose, such as Rayon. In another embodiment, the reservoir zone may comprise at least about 70 wt % of cellulosic fibers, preferably at least about 80 wt % and more preferably at least about 90 wt %. Alternatively, the reservoir zone may comprise from about 95 to 100 wt % cellulosic fibers.

In another embodiment, the reservoir zone may be in the form of a single or multi-ply tissue; a creped tissue; a tissue wadding; or an airfelt mat. High wet strength tissue may also be used as the reservoir zone. In another embodiment, the reservoir zone may be of any form having an open structure whereby the bodily fluids are held or absorbed in the fine interstitial spaces in the open structure. Further, inter-ply spaces and surface textures may provide additional interstitial, liquid holding capacities, which enhance the absorbency of the reservoir zone.

The reservoir zone may include supplemental chemical bonding agents that are well known in the art. For example, the reservoir zone may include a chemical bonding agent such as vinyl acrylic copolymers, polyvinyl acetate, crosslinkable polyamides, polyvinyl alcohol and the like. Additionally, wet strength resins and/or resin binders may be added to improve the strength of the cellulosic web. Useful binders and wet strength resins include commercially available resins, for example, KYMENE®, available from Hercules Chemical Company and PAREZ® available from American Cyanamid, Inc. Crosslinking agents and/or hydrating agents may also be added to the pulp mixture to reduce the degree of hydrogen bonding if an open or loose fibrous web is desired. An exemplary debonding agent is available from Quaker Chemical Company, Conshohocken, Pa., under the trade name Quaker 2008. The reservoir zone may contain no more than 5 weight percent and optionally may contain no more than about 2 weight percent of the chemical bonding agent. The reservoir zone typically comprises a high wet strength tissue. Alternatively, the reservoir zone may comprise a synthetic fibrous web. The reservoir zone may be bonded, such as with adhesives, to the barrier zone or other components of the diaper construction.

Suitable materials for the reservoir zone may comprise a primarily cellulosic fibrous web, such as commercially available consumer paper towels BOUNTY®, manufactured by The Procter & Gamble Company, Cincinnati, Ohio, or HI-DRY®, manufactured by The Kimberly-Clark Corporation.

Suitable fibrous webs may have a single-ply or a multi-ply construction. As used herein, the term "ply" means individual webs being disposed in a substantially contiguous, face-to-face relationship, forming a multiple layered web.

Further, a single web may form two plies, for example, by folding on itself. In a multi-ply construction, the individual webs are at least partially joined, typically via point bonding, with or without adhesives.

It is found that the multi-ply construction provides higher resistance to liquid breakthrough than a single-ply construction on a unit weight basis (gram per square meter). Further, the absorbency of a two-ply fibrous web is at least double that of the single-ply fibrous web, on a unit weight basis. Without being bound by theory, it is believed that the interstitial spaces (i.e., structural voids) between the plies provide additional liquid holding space, consequently, a higher absorptive capacity. Furthermore, post-treatments of the cellulosic web, including, but not limited to, aperturing, creping, embossing, or otherwise texturizing, increase the absorbency of the web. Fibrous webs having apertured or texturized surfaces show higher absorptive capacity, possibly due to the microvoids and/or interstitial spaces created by the treatments. In one embodiment, the reservoir zone is made from a fibrous web having a construction of at least two plies and a texturized surface. Additionally, certain additives, such as debonding agents, may also increase the absorbency of the web by reducing the inter-fiber bondings (e.g., hydrogen bonds between cellulosic fibers), thus, loosening the compacted fibrous network in the webs. The openness of the resulting web provides more interstitial spaces to hold liquids and enhances the absorbency of the web.

In an alternative embodiment, other types of wettable and/or hydrophilic fibrous materials may be used to form the reservoir zone of the absorbent barrier structure. Exemplary fibers include naturally occurring organic fibers made from intrinsically wettable material, such as cellulose or processed cellulose fibers, including regenerated or derivatized cellulose fibers commercially available as Rayon® fiber, Viscose® fibers; synthetic fibers made from inherently wettable thermoplastic polymers, such as polyesters, polyamides, their copolymers, polyvinyl alcohols, polyalkylene oxides, and mixtures of these polymers; and synthetic fibers made from a nonwettable thermoplastic polymers, such as polyethylene, polypropylene, polybutylene and other polyolefins, which may be hydrophilized by appropriate means. These nonwettable fibers may be hydrophilized by treatments with surfactants or surface-active agents having suitable hydrophilic functionalities, or by sheathing. These nonwettable fibers may also become of more wettable by grafting hydrophilic functionalities onto the polymer chains. Suitable hydrophilic functionalities include, but are not limited to, acrylic, methacrylic, ester, amide, and mixtures thereof. Combination fibers such as bi-component fibers, sheathed fibers, are also suitable for use herein.

The reservoir zone may contain additives such as chemical bonding agents, crosslinking agents, wet strength resins, debonding agents, liquid or moisture absorbing agents, odor absorbing agents, antimicrobials, coloring agents, stiffening agents, and mixtures thereof. The liquid or moisture absorbing agents, include, but are not limited to, clays, silicas, talc, diatomaceous earth, perlite, vermiculite, carbon, kaolin, mica, barium sulfate, aluminum silicates, sodium carbonate, calcium carbonate, other carbonates, superabsorbent polymers or other osmotic liquid holding agents, and mixtures thereof.

In one embodiment, the reservoir zone additionally contains superabsorbent polymers, which are coated onto the fibers, blended into the fibers in-situ, or are made into fibers or particles.

The Barrier Zone

The barrier zone preferably has a "barrier-like" property (i.e., resistance to liquid wet-through). The barrier property is typically measured by the Test Method B described below. It is desirable that the hydrohead value of the barrier zone should be higher than that of the absorbent core and of the reservoir zone. The barrier zone material suitable for use herein typically exhibits a hydrohead value of at least about 10 mBars, preferably at least about 30 mBars, more preferably at least about 50 mBars, and most preferably at least about 75 mBars. In some embodiments, the suitable barrier zone has a hydrohead value in the range from about 30 to about 100 mBars.

It is also desirable that the barrier zone substantially reduces the air/vapor permeability of the absorbent article. In that respect, the barrier zone typically has a convective air permeability of at least about 10 Darcy/mm and preferably at least about 30 Darcy/mm.

The hydrohead value of a fibrous web increases with finer fiber diameter, higher fiber density, higher basis weight, or combinations thereof. Suitable fibrous webs for the barrier zone typically have a basis weight of at least about 2 gsm, preferably from about 5 to about 100 gsm, more preferably from about 10 to about 75 gsm, and most preferably from about 15 to about 55 gsm.

The thickness of the barrier zone may vary, depending on the materials used, the properties desired, the intended use, the construction, and the like. Specifically, the thickness of the barrier zone may affect the air/gas permeability, the absorbency and/or leakage protection of the barrier absorbent structure, as well as the comfort and fit of the absorbent article, and like effects typically related to the thickness of a structure. Thus, the barrier zone typically has a thickness of less than about 1.5 mm, preferably less than about 1.0 mm, more preferably less than about 0.8 mm, and most preferably less than about 0.5 mm.

It has been found that some materials which do not appreciably limit the air permeability of the absorbent article in the dry state will significantly decrease the air permeability of the article when the absorbent core becomes loaded with liquids. Thus, suitable materials for use in the barrier zone should allow sufficient water vapor transmission, when the absorbent article is in a dry state. It is desirable that the air/water vapor permeability of the absorbent article does not change substantially from that of an equivalent diaper without the barrier zone material. However, when the absorbent core becomes loaded from absorbing liquids discharged from the body, the barrier zone may lower the air/vapor permeability of the absorbent article (relative to an equivalent article without a barrier zone), thereby reducing or eliminating the dampness which may develop on the garment side of the outer cover.

In order to provide the desired hydrohead value or the "barrier-like" property, suitable materials are preferably hydrophobic, though this is not a required characteristic. Exemplary hydrophobic polymeric materials are typically polyolefins, such as polyethylene, polypropylene, polybutylene and copolymers thereof. Materials that are not hydrophobic, such as polyamides, polyesters, polyalkylene oxides, polyvinyl alcohols, may be treated by suitable hydrophobic agents to achieve the desired hydrophobicity. Additionally, the reservoir layer may also be treated on at least one surface to improve its hydrophobicity, hence, its barrier property.

Treatments for improved hydrophobicity may include chemical, radiation, plasma or combinations thereof. Further, the surface treatment to modify the surface characteristics may be accomplished by a coating on the surface, by pre-blending with a hydrophobic agent or by incorporating a hydrophobic agent in-situ, which blooms to the surface by further processing.

In one embodiment, fluorocarbon treatment of the web material may provide the desired hydrophobicity such that the web exhibits the desired water resistance characteristics, measured, for example, by Test Method B. In another embodiment, fluorocarbon treatment using plasma or like technology may provide a very thin, hydrophobic coating such that the air permeability of the treated web is substantially unchanged. If desired, the treatment may be applied to only portions of the substrate surface. These treatments may be applied to different components of the absorbent article, including but are not limited to the barrier zone, the reservoir zone, the outer cover, or other diaper components. Suitable substrate materials for this treatment include, but are not limited to, nonwoven webs, cellulosic webs, thermoplastic films, modified/processed films (e.g., formed, apertured) and the like. Exemplary surface treatments using fluorocarbons are described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000; PCT Patent Application 99/20504 by D'Agostino et al., published on Sep. 7, 1999 (corresponding to U.S. Pat. No. 6,649,222); PCT Publication 00/14296 by D'Agostino et al., published on Mar. 16, 2000 (corresponding to U.S. Ser. No. 09/786075); the disclosures of each is hereby incorporated by reference.

Other surface coating methods using silicones or fluoro chemicals are known in the art and may be used herein. The conventional coating or surface treatment methods typically fill the voids within the web, and thus, lowers its air permeability. Coating methods to provide hydrophobicity to the substrate without the decrease in air permeability can be found in U.S. Pat. No. 5,322,729, the disclosure of which is hereby incorporated by reference.

The barrier zone may comprise fibrous web materials such as nonwoven webs including, but not limited to, meltblown (MB) webs; spunbond (SB) webs, particularly fine fiber spunbond webs such as those having fiber deniers of about 2 or less; composite webs having layers of meltblown and spunbonded fibers, commonly known as MS nonwovens, and SMS nonwovens; bonded and carded webs; air laid webs; hydro-entangled webs; knitted webs; and woven webs.

Nonwoven webs having the desired combination of high liquid resistance and high air permeability are typically made by the melt blowing process. Nonwoven webs comprising low denier fibers and/or uniform distribution of fine fibers are desirable.

In one embodiment, the barrier zone comprises a meltblown web of polypropylene fibers having a basis weight of from about 4 to about 80 g/m$^2$, preferably from about 6 to about 70 g/m$^2$, more preferably from about 8 g/m$^2$ to about 50 g/m$^2$, and most preferably from about 10 to about 30 g/m$^2$.

The meltblown fibers typically have an average diameter in the range of less than about 20 microns, preferably less than about 10 microns. Most typically, the meltblown fibers have an average fiber diameter in the 5 to 10 microns range. Also suitable for use herein are nanofibers having an average fiber diameter in the range of less than about 500 nanometers, preferably less than about 300 nanometers, and more preferably less than about 150 nanometers. Exemplary nonwoven webs made from nanofibers (having average fiber diameters from about 10 to about 100 nanometers) are available from E-Spin Technologies (Chananooga, Tenn.).

While the strength of the meltblown nonwoven web generally decreases with decreasing fiber denier, the strength can be improved by lamination with a reinforcing scrim or web such as tissues, paper towels, or spunbonded nonwoven webs. Any conventional lamination process may be used, including adhesive bonding, thermal boning, ultrasonic bonding, calendaring, needling, and combinations thereof. However, the lamination process should be carefully exercised to minimize adverse effects on the air permeability of the resulting laminate. In one embodiment, the microfiber nonwoven web may be integrally laminated during the manufacture by direct melt blowing onto another reinforcing scrim or web.

The fibrous barrier zone may comprise a single web or multiple layers of webs which collectively have the desired characteristics. However, when using multiple layers of webs, it is desirable that they are juxtaposed without being point bonded across a substantial surface area of the zones or otherwise bonded in a manner which would substantially limit the breathability of the zones. When joining the barrier zone to the absorbent core and/or the reservoir zone, it is desirable that the breathability of the article is maintained. In this regard, it may be desirable that the barrier zone be attached to other components the absorbent article (such as the absorbent core, the reservoir zone) primarily at the peripheries of the barrier zone. The multiple zones can be joined by heat, pressure, ultrasonic, adhesive or by other means known in the art.

The barrier zone may contain additives such as chemical bonding agents, crosslinking agents, liquid or moisture absorbing agents, odor absorbing agents, antimicrobials, coloring agents, stiffening agents, and mixtures thereof. The liquid or moisture absorbing agents, including, but not limited to, clays, silicas, talc, diatomaceous earth, perlite, vermiculite, carbon, kaolin, mica, barium sulfate, aluminum silicates, sodium carbonate, calcium carbonate, other carbonates, superabsorbent polymers or other osmotic liquid holding agents, and mixtures thereof.

Absorbent Article Components

FIG. 1 is a partially broken top plan view of a diaper 20 containing the absorbent barrier structure 10 of the present invention. The diaper 20 is in a flat-out state with portions of the structure cut away to more clearly show the construction of the diaper 20. The garment-facing surface of the diaper 20 is oriented away from the viewer.

As shown in FIG. 1, the diaper 20 comprises a liquid pervious topsheet 24; a dampness management means 26; an absorbent core 28, which is positioned between at least a portion of the topsheet 24 and the outer cover 22; an absorbent barrier structure 10 positioned between the absorbent core 28 and the outer cover 22; side panels 30; elasticized leg cuffs 32; elastic waist features 34; and a fastening system 40. An absorbent barrier structure 10 of the present invention is disposed adjacent to the absorbent core 28 on the garment facing surface of the absorbent core 28.

Diaper 20 is shown in FIG. 1 to have a front waist region 36, a rear waist region 38 opposed to the front waist region 36 and a crotch region 37 located between the front and the rear waist regions. The peripheries of the diaper 20 are defined by the outer edges of the diaper 20 in which the longitudinal edges 50 run generally parallel to the longitudinal centerline 100 of the diaper 20 and end edges 52 run between the longitudinal edges 50 generally parallel to the lateral centerline 110 of the diaper 20.

The main body of the diaper 20 comprises at least the absorbent core 28, the topsheet 24, and preferably, though not necessarily, the dampness management means 26. An outer cover 22 forms the chassis, onto which other components of the diaper 20 are added to form the unitary structure of the diaper.

FIG. 1 shows an embodiment of the diaper 20 in which the topsheet 24 and the dampness management means 26 have length and width dimensions generally no smaller than those of the absorbent core 28 and the absorbent barrier structure 10. The topsheet 24 and the dampness management means 26 may extend to the peripheries of the diaper 20. In another embodiment, the absorbent barrier structure 10 may extend beyond the edges of the absorbent core 28 to the peripheries of the diaper 20.

While the components of the diaper 20 may be assembled in various well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

Topsheet or Body-Side Liner

The topsheet is compliant, soft feeling, and non-irritating to the wearer's skin. The topsheet material can also be elastically stretchable in one or two directions. Further, the topsheet is fluid pervious, permitting fluids (e.g., urine, menses, other bodily fluids) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof.

Preferred topsheets for use in the present invention are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. No. 5,628,097, U.S. Pat. No. 5,916,661, EP 1,051,958 (corresponding to U.S. Pat. No. 6,706,946), EP 1,076,539 (corresponding to U.S. Pat. No. 6,545,197); the disclosure of each is hereby incorporated by reference.

Nonwoven materials, such as described in EP 774,242 (corresponding to U.S. Pat. No. 6,107,539) (Palumbo), which is incorporated herein by reference, generally exhibit high gas permeability, thus, do not exhibit a significant resistance to air flow.

Further, suitable tosphleet materials for depositing solid excretions thereon may include nonwovens having apertures, which are at least in the portions that are aligned with the feces deposition region of the article. Suitable apertured nonwovens are described in more detail in EP 714,272 (corresponding to U.S. Pat. No. 6,414,215) or EP 702,543 (corresponding to U.S. Pat. No. 5,342,338), and both of which are incorporated herein by reference. In another embodiment of feces handling articles, such topsheets can be combined with feces handling members e.g. underlying such topsheets, and further described in these applications.

The material forming the topsheet may be hydrophilic so as to facilitate fluid transport through the topsheet. Surfactants may be incorporated into the polymeric materials to improve the hydrophilicity of the topsheet, such as is disclosed in EP-A-166,056 (corresponding to U.S. Pat. No. 4,647,448) and U.S. patent application Ser. No. 07/794,745, filed on Nov. 19, 1991, both of which are incorporated herein by reference. Alternatively, the topsheet may be treated with a surfactant to render the body-facing surface hydrophilic, such as is disclosed in U.S. Pat. No. 4,950,254, which is hereby incorporated by reference.

Absorbent Core

The absorbent core may include the following components: (a) optionally, a primary fluid distribution layer; (b) optionally, a secondary fluid distribution layer; (c) a fluid storage layer; (d) other optional components, such as a fibrous "dusting" layer.

The optionally primary fluid distribution layer is typically disposed under the topsheet and is in fluid communication with the topsheet. The topsheet transfers the acquired bodily fluids to the primary distribution layer to ultimate distribution to the storage layer. This transfer of fluid through the primary distribution layer occurs not only in the thickness, but also along the length and width directions of the absorbent core. The optionally secondary fluid distribution layer is typically disposed under the primary fluid distribution layer and is in fluid communication therewith. The secondary fluid distribution layer readily acquires fluid from the primary distribution layer and transfers it rapidly to the underlying storage layer. Thus, the fluid capacity of the underlying storage layer may be fully utilized, especially when gushes of bodily discharge occur.

The fluid storage layer typically comprises absorbent materials including absorbent gelling materials, which are usually referred to as "hydrogels", "superabsorbent" "hydrocolloid" materials. Absorbent gelling materials are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such are fibers, foams, sheets, strips, or other macrostructures, are also suitable for use herein. Suitable absorbent gelling materials in the form of open cell foams may include those disclosed in U.S. Pat. No. 3,563,243 (Lindquist), U.S. Pat. No. 4,554,297 (Dabi), U.S. Pat. No. 4,740,520 (Garvey), U.S. Pat. No. 5,260,345 (DesMarais et al.), all of which are incorporated herein by reference. Improvements of these foams can be found in WO 96/21679 (corresponding to U.S. Pat. No. 5,500,451), WO 96/21680 (corresponding to U.S. Pat. No. 5,650,222), WO 96/21681 (corresponding to U.S. Pat. No. 5,563,179), WO 96/21682 (corresponding to U.S. Pat. No. 5,795,921), WO 97/07832 (corresponding to U.S.

Pat. No. 5,550,167) and WO 98/00085 (corresponding to U.S. Pat. No. 5,873,869), all of which are incorporated herein by reference.

The absorbent gelling materials suitable for use herein may comprise a substantially water-insoluble, slightly crosslinked, partially neutralized, polymeric gelling material. This material forms a hydrogel upon contact with water. Suitable absorbent gelling materials include those disclosed in U.S. Pat. No. 4,654,039, U.S. Pat. No. 5,562,646, U.S. Pat. No. 5,599,335, U.S. Pat. No. 5,669,894, each of which is incorporated herein by reference.

The fluid storage layer may comprise absorbent gelling materials alone or dispersed in a suitable carrier, homogeneously or inhomogenously, or may comprise of absorbent carrier materials alone. The storage layer may also include filler materials, such as perlite, diatomaceous earth, vermiculite, and the like, which absorb and retain the fluid, and thus, reduce the rewet-through the topsheet.

Suitable carrier materials include cellulose fibers, in the form of fluff, tissues or paper. Modified cellulose fibers (e.g., stiffened, chemically treated, crosslinked) may also be used. Synthetic fibers may also be used. Suitable synthetic fibers may be made of cellulose acetate, polyvinyl fluoride, polyvinylidene chloride, acrylics (such as Orlon®), polyvinyl acetate, non-soluble polyvinyl alcohol, polyethylene, polypropylene, polyamides (such as Nylon®), polyesters, bi- or tri-component fibers thereof, and mixtures of these materials. Preferably, the fiber surfaces are hydrophilic or are treated to be hydrophilic.

Typically, the storage layer comprises from about 15 to 100 wt % of the absorbent gelling material dispersed in a carrier material. Preferably the storage layer comprises from about 30 to about 95 wt %, more preferably from about 60 to about 90 wt % of the absorbent gelling material. The carrier material typically comprises from about 0 to about 85 wt %, preferably from about 5 to about 70 wt %, and more preferably from about 10 to about 40 wt % of the storage layer.

An optional component for inclusion in the absorbent core is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Further, the "dusting" layer provides some additional fluid handling capability such as rapid wicking of fluid along the length of the absorbent core.

The absorbent core may include other optional components. For example, a reinforcing scrim may be positioned within the respective zones, or between the respective zones, of the absorbent core. Optionally, odor control agents may be included in the absorbent core. Suitable odor control agents include active carbons, zeolites, clays, silicas, and mixtures thereof. The configuration and construction of the absorbent core may also be varied (e.g., the absorbent core may have varying caliper zones, a hydrophilicity gradient, a pore size gradient, a superabsorbent gradient, or lower average density and lower average basis weight acquisition zones; or may comprise one or more zones or structures). The total absorbent capacity of the absorbent core should, however, be compatible with the designed loading and the intended use of the diaper. Further, the size and absorbent capacity of the absorbent core may be varied to accommodate wearers ranging from infants through adults. Suitable absorbent cores include those disclosed in EP 1,051,958 (corresponding to U.S. Pat. No. 6,706,946), EP 797,968 (corresponding to U.S. Pat. No. 6,388,166) and EP 774,242 (corresponding to U.S. Pat. No. 6,107,539), each of which is incorporated by reference herein.

Outer Cover

The term "outer cover" as used herein means a structural element positioned on the garment-facing surface of the absorbent article. The outer cover typically forms the chassis onto which other components of the diaper are added. However, the outer cover may just be a coating layer on the garment side of the absorbent article.

Suitable material for the outer cover typically provide a barrier function with respect to liquids (i.e., liquid impervious) while preferably allowing air or vapor to flow through (i.e., vapor permeable). Typically, the outer cover is not the rate limiting element to gas or vapor transport through the absorbent article. In some embodiments, the outer cover may have a structure that is relatively open to allow for convective air or gas permeability. The suitable outer cover typically has a moisture vapor transmission rate (MVTR) of at least about 500 $g/m^2/24$ hrs, more preferably of at least about 1500 $g/m^2/24$ hrs, and most preferably at least about 3000 $g/m^2/24$ hrs. Additionally, the outer cover provides a soft, pleasant feel to the skin, either by the material property, or by texturizing or embossing its surface, or both.

The outer cover may be a single layer of homogeneous or multi-component material, or a composite of various layers of materials. The outer cover suitable for use herein comprises porous materials such as an apertured film (e.g., having a plurality of shaped openings or angled capillaries), a knitted web, a porous woven or nonwoven web, a foam, or combinations or laminates thereof. In one embodiment, the outer cover comprises nonwoven webs or multi-layered nonwovens such as spunbond/meltblown (SB) nonwoven, spunbond/meltblown/spunbond (SBS) nonwoven.

The outer cover, or any portion thereof, may be elastically extensible in one or more directions. In one embodiment, the outer cover may comprise a structural elastic-like film ("SELF") web. A SELF web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, which is incorporated herein by reference. In alternate embodiments, the outer cover may combine elastomeric components (such as films, foams, strands, or combinations thereof) with nonwovens or synthetic films.

In another embodiment, the outer cover may be a nonwoven web constructed to provide the required level of liquid impermeability. For example, a nonwoven web of spunbonded or meltblown polymer fibers may be treated, at least partially, with a hydrophobic coating. Exemplary treatments using fluorocarbons are described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000; U.S. Patent Application Ser. No. 99/20504 by D'Agostino et al., filed on Mar. 7, 1999; the disclosures of which are hereby incorporated by reference.

Optionally, the outer cover material may comprise the absorbent and swellable materials described in U.S. Pat. No. 5,955,187 issued to McCormack et al. on Sep. 21, 1999; or the absorbent and shrinkable materials described in U.S. Patent Application Serial no. 97/22604 by Corzani et al. on Dec. 15, 1997; or the absorbent and differential strainable materials described in PCT Publication WO 00/68003 by Dawson et al. (corresponding to U.S. Pat. No. 6,770,579); the disclosures of which are hereby incorporated by reference.

The absorbent article may comprise an outer cover which is separated from the absorbent core at least partially by the absorbent barrier structure of the present invention and is preferably joined to the absorbent barrier structure and/or the absorbent core by attachment means such as those well known in the art.

The outer cover may be secured to the absorbent barrier structure and/or the absorbent core by a uniform continuous layer of adhesive, an open pattern network of filaments of adhesive, or an array of separate lines, spirals, or spots of adhesive, as disclosed in U.S. Pat. No. 4,573,986 issued to Minetola et al. on Mar. 4, 1986; U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989; the disclosure of each is incorporated herein by reference. Adhesives suitable for use herein are manufactured by H.B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The outer cover material may not significantly lower the convective air permeability of the absorbent article. More importantly, the combination of the absorbent barrier structure and the outer cover (hereinafter referred to as the "combined structure" or "combination") provide the desired balance of properties, including, but not limited to, absorbency, barrier property and convective air permeability.

The combined structure of the present invention may be constructed to have a convective air permeability of at least about 10 Darcy/mm, preferably at least about 20 Darcy/mm, more preferably at least about 30 Darcy/mm, and most preferably at least about 50 Darcy/mm. Convective air permeability is especially effective in removing moisture vapor from inside the absorbent article, resulting in a lower humidity in the local environment next to the skin, which reduces incidences of skin irritation or rash and promotes skin health.

Further, the combined structure of the present invention preferably has a liquid impact transmission value (as measured by Test Method C) of no more than about 10 $g/m^2$, more preferably no more than about 8 $g/m^2$, and most preferably no more than about 5 $g/m^2$.

Moreover, the combined structure should exhibit a hydrohead value of at least about 20 mBars, preferably at least about 35 mBars, more preferably at least about 50 mBars, and most preferably at least about 75 mBars.

In a preferred embodiment, the combined structure of the present invention exhibits desired leakage protection or barrier properties at least equal to that of the absorbent barrier structure.

Dampness Management Means

Optionally, as shown in FIG. 1, a dampness management means 26 may be included in the absorbent article of the present invention. The dampness management means 26 may provide further leakage protection. Suitable materials for dampness management means 26 are breathable materials which permit vapors to escape from the diaper 20. Exemplary materials may include apertured films; monolithic or microporous films, preferably with apertures; modified (with respect to pore structures and distributions) nonwovens or composite materials such as film/nonwoven laminates.

Suitable apertured films typically have open surface area at least about 1%, preferably at least about 5% more preferably at least about 10%. In another embodiment, the open surface area may be 0.1% or more, provided there are sufficient amount of relatively large pores present. Further, suitable apertured films should have an open surface area less than about 20% such that it would have insubstantial effect on the leakage protection properties of the article. Apertured films may be vacuum formed or hydro-formed to provide macro and/or micro apertures. More detailed descriptions of suitable apertured films can be found in U.S. Pat. No. 4,629,643, U.S. Pat. No. 4,609,518 and U.S. Pat. No. 4,695,422, U.S. Pat. No. 4,342,314 and U.S. Pat. No. 4,463,045; the disclosure of each is incorporated by reference herein.

In another embodiment, the dampness management means may include zones of different breathability and/or liquid permeability. For example, the dampness management means may be higher in breathability and/or liquid permeability in zones which do not coincide with the absorbent core. As used herein, the term "breathability" refers to the diffusive transport of water vapor through the material. The dampness management means may be assembled of one or more layers and preferably includes at least one layer which is liquid impermeable, the liquid impermeable layer preferably located adjacent the absorbent core and preferably covers an area at least as large as the absorbent core.

Further, moisture condensation on the outer surface (i.e., the garment side) of the absorbent article leads to dampness to the touch, which reduces wearer comfort and is often perceived as a performance problem with the article. The convective transport of moisture vapor through the absorbent article of the present invention is very effective such that it may lead to moisture condensation on the outer surface of the article and the perceived dampness problem. Thus, it may be beneficial to incorporate a relatively low breathability dampness management means into the article of the present invention. Suitable low breathability dampness management means should have a MVTR of no more than about 4500 $g/m^2/24$ hrs, preferably of no more than about 3500 $g/m^2/24$ hrs, more preferably no more than about 3000 $g/m^2/24$ hrs, and most preferably no more than about 2500 $g/m^2/24$ hrs.

The dampness management means may be disposed between the outer cover and the absorbent barrier structure of the present invention. Alternatively, the dampness management means may be disposed within the absorbent barrier structure between the absorbent layer and one or both of the barrier layers.

Other Components

In addition, the diaper, as represented in FIG. 3, may further include a pair of fasteners 40 which are employed to secure the diaper about the waist of the wearer. Suitable fasteners include hook-and-loop type fasteners, adhesive tape fasteners, buttons, snaps, mushroom-and-loop fasteners and the like. The diaper of the present invention may also include elasticized leg bands which help secure the diaper to the wearer and, thus, help reduce leakage from the diaper. Similarly, it is also known to include a pair of elasticized, longitudinally extending containment flaps which are configured to maintain a substantially upright, perpendicular arrangement along the central portion of the diaper to serve as an additional barrier to the lateral flow of body exudates.

It is also common to include a surge management layer positioned between the topsheet and the absorbent core in order to help prevent pooling of fluids on the portion of the diaper adjacent the wearer's skin.

The articles of the present invention may also include waste management features, such as pockets for receiving and containing waste, spacers which provide voids for waste, barriers for limiting the movement of waste in the article, compartments or voids which accept and contain waste materials deposited in the diaper 20, and any combinations thereof.

Optionally, the absorbent articles of the present invention may include a skin care composition, preferably on the skin-contacting surfaces of the article. The skin care composition useful herein is directed to maintain and/or improve the skin condition of the skin under an absorbent article or skin that is subjected to chronic or acute exposures to body exudates, moisture, irritants, etc. It is preferred that the skin care composition provides a protective, and preferably non-occlusive function (e.g., a relatively liquid impervious but vapor pervious barrier) to avoid skin overhydration and skin exposure to materials contained in body exudates (e.g., urine, feces, menstrual fluids). It is also preferable that the skin care composition provides an abrasion minimizing function to reduce skin irritation in the areas where the absorbent article is in contact with the wearer's skin. Additionally, the skin care composition may contain skin care ingredients, which directly or indirectly, deliver skin care benefits, such as reduction of overhydration, reduction of redness, skin conditioning, and removal or reduction of skin irritants in body exudates. It is also preferred that the skin care composition contains emollients that protect or improve the skin against chaffing, roughness, wrinkled appearance or itchiness. The skin care composition may also contain skin soothing agents, such as aloe vera, and chamomile.

Skin care compositions suitable for use in the present invention are described in U.S. patent application Ser. Nos. 08/926,532 and 08/926,533, each filed on Sep. 10, 1997; U.S. patent application Ser. Nos. 09/041,509, 09/041,232 and 09/041,266, each filed on Mar. 12, 1998; U.S. patent application Ser. No. 09/563,638, filed on May 2, 2000; U.S. Pat. No. 5,607,760 issued Mar. 4, 1997; U.S. patent application Ser. No. 09/466,343, filed on Dec. 17, 1999; U.S. Pat. No. 5,609,587 issued Mar. 11, 1997; U.S. Pat. No. 5,635,191 issued Jun. 3, 1997; U.S. Pat. No. 5,643,588 issued Jul. 1, 1997; and U.S. Pat. No. 6,153,209 issued Nov. 28, 2000; the disclosures of which are hereby incorporated by reference.

Making the Absorbent Barrier Structure

In one embodiment, the nonwoven web and the cellulosic web forming the absorbent barrier structure are adhesively bonded together using Ato-Findley adhesive H2031F. The nonwoven web is unwound from a supply roll and advances to the spray station where the adhesive is pre-heated to its melt state and sprayed (using a DYNATEC® spray head) onto the web substrate before the nonwoven web is assembled with the cellulosic web to form the absorbent barrier structure. The adhesive forms three continuous stripes along the longitudinal direction of the advancing web. The stripes are substantially parallel. Each stripe is 22 mm in width and the outer stripes are about 4 mm from the peripheries of the web.

In another embodiment, the first nonwoven web and the cellulosic web may be adhesively joined together according to the method described above. A second nonwoven web is unwound from a supply roll, spray-coated with adhesives, then joined to the free surface of the cellulosic web. In another three-layered absorbent barrier structure, the two nonwoven webs may be unwound from separate supply rolls and spray-coated with adhesives, then simultaneously joined to the opposed surfaces of the cellulosic web.

The absorbent barrier structure may be incorporated into a disposable diaper having the general construction as the diaper shown in FIG. 1 following well-known assembly processes. Typically, the absorbent barrier structure is disposed between the absorbent core and the outer cover. In a two-layered construction, the barrier layer is disposed adjacent to the garment-facing side of the absorbent core and the absorbent layer is disposed adjacent to the outer cover. In a three-layered construction, the first barrier layer is disposed adjacent to the garment-facing side of the absorbent core and the second barrier layer is disposed adjacent to the outer cover. Other well known components may be incorporated within the diaper without departing from the spirit of the present invention. Further, the manner and method of using these well known components in connection with the absorbent article of the present invention will likewise be readily appreciated by those skilled in the art.

Test Methods

A. Air Permeability

The air permeability is determined by measuring the time in which a standard volume of air is drawn through the test specimen at a constant pressure. This test is particularly suited to materials having relatively high permeability to gases, such as nonwovens, apertured films and the like.

A TexTest FX3300 instrument (available from Advanced Testing Instruments, Corp., Spartanburg, S.C.) is used. The Test Method conforms to ASTM D737. The test is operated in a laboratory environment typically about 22±2° C. and about 35±15% relative humidity. The test specimen is kept in this laboratory environment for at least 2 hours prior to testing. The test pressure is 125 Pascals and the test area is 38 cm². In this test, the instrument creates a constant differential pressure across the sample which draws air through the sample. The rate of air flow through the sample is measured in ft³ per min per ft² (ft³/min/ft²) and converted to permeance (in Darcy/mm) according to the Darcy's Law:

$$K/d(\text{Darcy/mm}) = (V \cdot \mu)/(t \cdot A \cdot \Delta p)$$

wherein K is the permeability per unit area of the specimen; V/t is the volumetric flow rate in cm³/sec; $\mu$ is the viscosity of air (1.86·10⁻⁵ Pa sec); d is the test material thickness in mm; A is the cross sectional area of the specimen in cm²; $\Delta p$ is the pressure differential in Pascal or Pa; and 1 Darcy=9.869·10⁻⁹ cm².

For each sample, three replicates should be run, and the averaged result is reported.

B. Hydrostatic Head (Hydrohead) Pressure Test

This property determined by this test is a measure of the liquid barrier property (or liquid impermeability) of a material. Specifically, this test measures the hydrostatic pressure supported by the material at the point when water penetration through the material first occurs.

A TexTest Hydrostatic Head Tester FX3000 (available from Advanced Testing Instruments, Corp., Spartanburg, S.C.) is used. The test method conforms to Edana 120.1-18. For this test, pressure is applied to a defined sample portion and gradually increases until water penetrates through the sample.

The test is conducted in a laboratory environment typically about (22±2° C.) and a relative humidity of about 35±15%. The test specimen is kept in this laboratory environment for at least 2 hours prior to testing. The sample is clamped over the top of the water reservoir of the instrument, using gasketing material to prevent side leakage during testing. When testing an absorbent barrier structure of the present invention, which comprises a layer of a barrier material and a layer of a reservoir material, the sample is oriented such that the layer of the barrier material faces the water during the test. The area of water contact with the sample is 28 cm$^2$.

The water pressure is increased at a rate of 3 mBar/min. Thus, the sample is subjected to a steadily increasing water pressure on the surface of the barrier layer. When water breakout appears on three locations on the top surface of the sample, the pressure at which the third breakout occurs is recorded. For some samples, the water breakouts at various locations may occur contemporaneously, the pressure at the instant the breakouts occur is recorded. If water immediately penetrates the sample (i.e., the sample provided no resistance), a zero reading is recorded. For each material, three specimens are tested and the results are averaged.

C. Liquid Impact Transmission Test

The properties determined by this method correlate with the fluid resistance capability under sudden impact, which relates to leakage protection, provided by the absorbent structure of the present invention. In this test, a sample of the absorbent structure is layered with a loaded absorbent core simulant, and the combination is subjected to an impact force. The properties determined by this method is relevant to the actual use condition where the wearer (especially a baby) falling from a standing position, thus, applying an impact force on a loaded diaper.

Figure 5A:
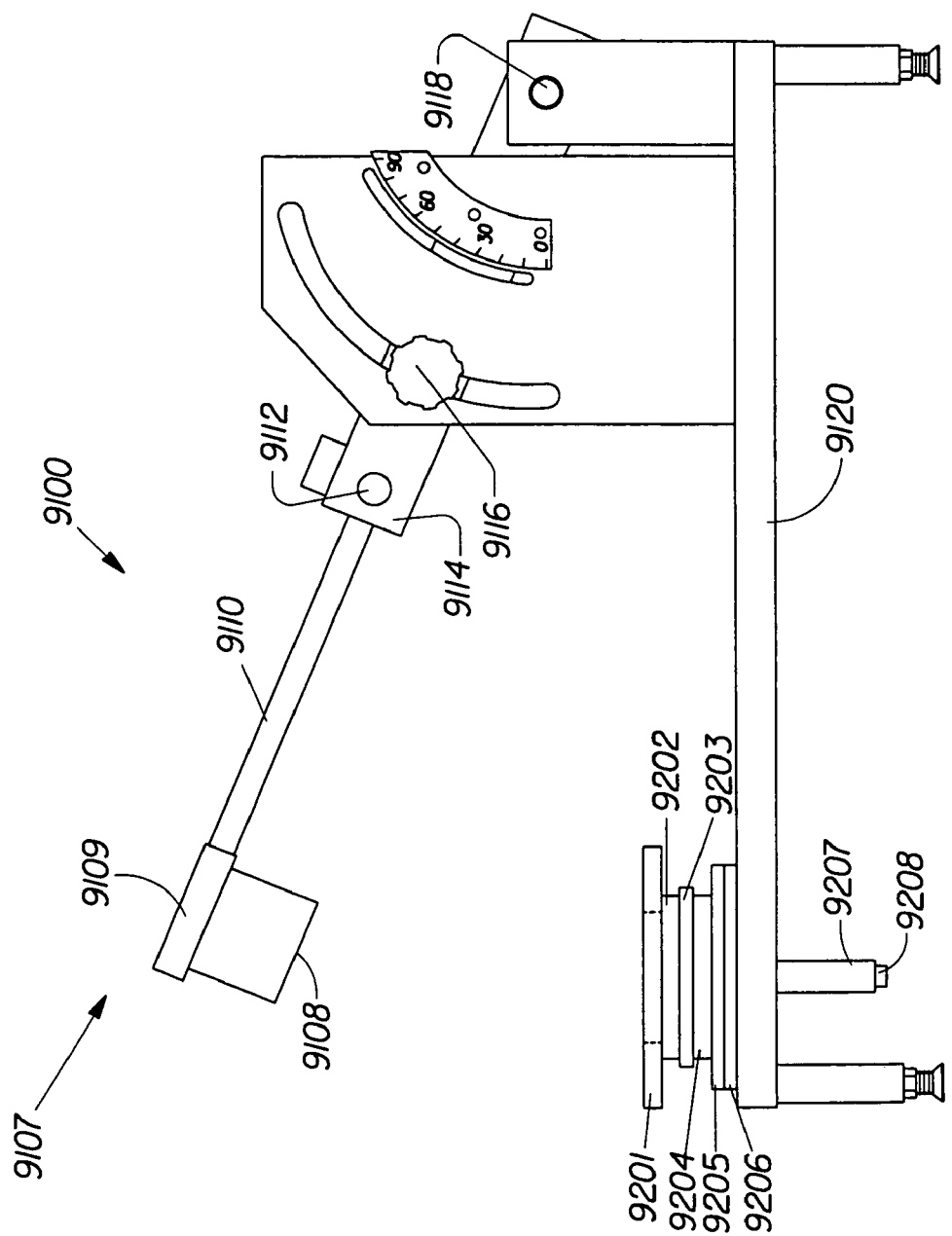
FIGS. 5A–5B are schematic illustrations of the liquid impact tester before and during the test.
Figure 5B:
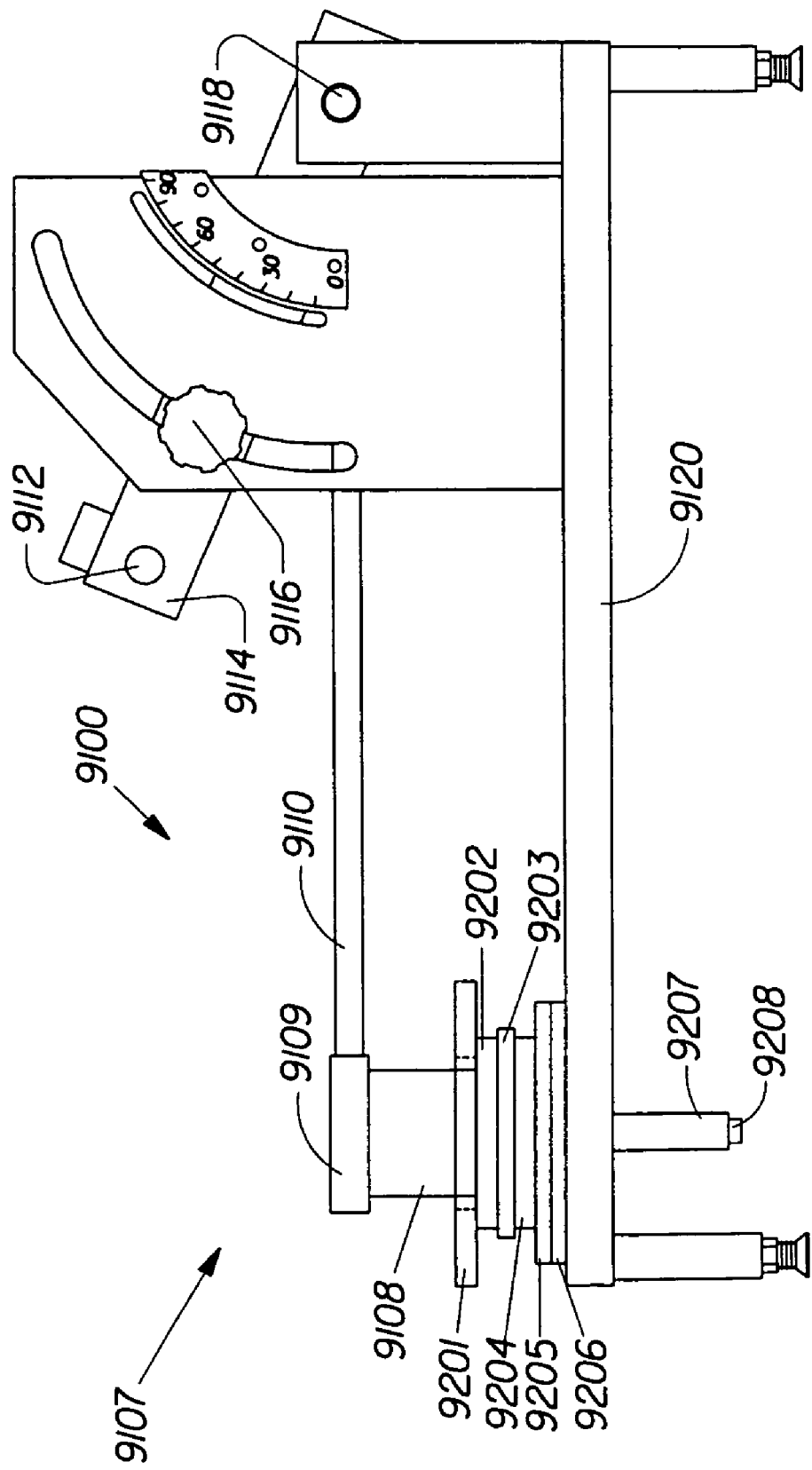

Liquid impact transmission test is measured with the apparatus 9100 shown in FIGS. 5A and 5B. The receiving table 9120 is supported by four adjustable legs, which level the receiving table 9120. The impact assembly includes a head 9107 and an arm 9110. The head 9107 includes a hammer 9108 (a metal cylinder of 63 mm in diameter) mounted on a base plate 9109. The arm 9110 is attached to the base plate 9109 on one end and is pivotally attached to hinge 9118 on the other end. The length from hinge 9118 to the distal end of the base plate 9109 is about 551 mm. The arm 9110 is attached to a mounting piece 9114 by a release pin 9112. The mounting piece 9114 is positioned (by knob 9116) at a desired (typically 30°) angle with respect to the horizontal table 9120.

An energy absorbing impact pad 9205 is 12.7 cm by 12.7 cm (5 inches by 5 inches) and 0.79 cm (0.3125 inches) thick. The energy absorbing impact pad 9205 is made of silicone rubber sheeting (Part no. 8632 K37, available from McMaster Carr of Cleveland, Ohio). The energy absorbing impact pad 9205 is attached to a metal plate 9206 of the same dimension. The metal plate 9206 is supported by a shock absorber 9207 (Model MA 600 from Ace Controls, Inc., Farmington, Mich.). The bottom surface of the metal plate 9206 is about 10 mm above the receiving table 9120 in the starting position (FIG. 5A). The adjustment knob 9208 of the shock absorber 9207 is set (at about 5) to smooth the deceleration throughout the stroke. When properly set-up, the hammer 9108 renders a dead blow (i.e., no observable rebound) on the sample assembly.

An absorbent core simulant 9204 is placed is centrally placed on top of the energy absorbing impact pad 9205. The absorbent core simulant 9204 comprises four layers of No. 4 filter paper (70 mm diameter) available from Whatman Laboratory Division, Distributed by VWR Scientific of Cleveland, Ohio. The core simulant 9204 is evenly loaded with 2 grams of simulated urine. The simulated urine is an aqueous 0.9% by weight saline solution, exhibiting a surface energy value of 72.5 mN/m as conventionally determined.

Sample 9203 is a barrier absorbent structure of the present invention that includes a barrier zone and a reservoir zone arranged in layers. Sample 9203 is centrally placed over the core simulant 9204, with the barrier layer facing the core simulant 9204. The surface area of the core simulant 9204 and sample 9203 are slightly larger than the surface area of block 9108, which is 63 mm in diameter (0.003117 m$^2$ in area).

An absorbent material 9202 is weighed to the nearest 0.0001 gram and placed on top of sample 9203 to absorb and retain simulated urine, which passes through sample 9203. The absorbent material 9202 comprises a No. 4 filter paper (70 mm diameter) available from Whatman Laboratory Division.

A weight 9201 is centrally placed on top of absorbent material 9202 to weigh down the sample assembly. The weight 9201 is made of Plexiglas, measures 5" by 5" (12.7 cm by 12.7 cm) and weighs about 206 gm. The weight 9201 has a circular hole in the center whose diameter (75 mm) is slightly larger than the diameter of the hammer 9108. When arm 9110 is released, hammer 9108 strikes through the central hole in weight 9201 and renders a dead blow on the central portion of the sample assembly.

In the pre-test position (FIG. 5A), the arm assembly is held at the same angle as the mounting piece 9114 by release pin 9112. To initiate the impact test, the release pin 9112 is pulled, whereby arm 9110 changes from a starting position, as shown in FIG. 5A, to a horizontal final position, as shown in FIG. 5B. A stop watch is activated upon impact to time the experiment.

In the particular set-up described above, hammer 9108 reaches an acceleration of 70 times gravity when the metal plate 9206 touches the receiving table, thereby initiating the deceleration. Thus, the impact assembly applies an impact force of 2060 Newtons (according to the formula: force=weight*acceleration) on the sample assembly. An accelerometer (model 353B02, available from PCB Piezotronics, Inc. Depew, N.Y.) may be used to measure the acceleration. To obtain the weight, the release pin 9112 is pulled to free the impact assembly from the mounting piece 9114; then, the receiving table 9120 is tilted to the position that places arm 9110 in a horizontal position and hammer 9108 resting on a top-loading balance. The weight registered on the balance is used in the formula above. For the particular set up used herein, the weight is about 3 kg. The weight and length of the impact assembly as well as the angle of the mounting piece 9114 may be different from those specified above, so long as these elements together provide an impact force of 2060 Newtons upon impact.

The impact assembly is then allowed to rest in this horizontal position for two minutes. The arm 9110 is raised and the filter paper 9202 is removed and placed on a balance. The weight of the filter paper 9202 at three-minutes from impact is recorded. The Liquid Impact Transmission (LIT) value is calculated and expressed in grams/m$^2$ using the following formula:

$$LIT=[\text{final weight of the filter paper}-\text{initial weight of the filter paper}]/[\text{impact area}]$$

wherein the impact area, expressed in m², is the area of the core simulant 9204 (about 0.003848 m²). For each material, three specimens are tested and the averaged result is reported.

D. Static Liquid Transmission Test

The property determined by this test correlates with the fluid retaining ability (or leakage protection) provided by the absorbent barrier structure of the present invention under an impact and sustained pressure condition. The property determined by this test is relevant to the actual use condition where the wearer suddenly moves from a standing position to a second position (e.g., sitting), and maintains the second position for an extended time period.

The equipment and sample set-up are the same as those described above in the Liquid Impact Transmission Test, except in this test, arm 9110 is dropped to deliver an impact force of 2060 Newtons and is allowed to rest on the sample for a set period of time (the "hold time"). Arm 9110 is then raised, the filter paper 9202 is removed and weighed, and the change in weight is reported as described above. The hold times at the horizontal resting position are 2, 5, 8, 15, 30 and 60 minutes.

E. Moisture Vapor Transmission Rate

The Moisture Vapor Transmission Rate (MVTR) determines the amount of moisture adsorbed by calcium chloride in a "cup" like container that is covered by a test specimen. The moisture source is a controlled temperature and humidity environment (40±3° C. and 75±3% relative humidity) separated from the calcium chloride by the test specimen. This method is applicable to test specimens such as thin films, multi layer laminates and the like.

The sample holding cup is a cylinder with an inner diameter of 30 mm and an inside height from bottom to top flange of 49 mm. A flange having a circular opening to match the opening of the cylinder can be fixed by screws, and a silicone rubber sealing ring with an opening matching the inner diameter of the cup fits between the top flange and the cylinder. The test specimen is positioned such that it covers the cylinder opening. The specimen is securely fixed between the silicone rubber sealing and the upper flange of the cylinder so it acts as a barrier to moisture transport.

The equipment as well as the test specimen should be equilibrated (about two hours or more) to the temperature of the controlled environment prior to testing.

The absorbent desiccant material is $CaCl_2$, such as can be purchased from Wako Pure Chemical Industries Ltd., Richmond, Va. under the product designation 030-00525. If kept in a sealed bottle, it may be used directly. It may be sieved to remove lumps or fines, if existing. It may also be dried at 200° C. for about 4 hours prior to use.

The $CaCl_2$ is poured into the cup. The cup is tamped down 10 times. Then a spacer is used to set a 1 cm gap between the top of the $CaCl_2$ and the top of the cup.

A test sample, cut to about 3.2 cm by 6.25 cm, is placed flat and overlapping the opening of the cup. The silicone rubber seal and the flange are placed on top of the sample and aligned with the screw holes and are affixed by the screws without over tightening. The total weight of the cup assembly is accurately recorded to three decimal places, and the assembly is placed into the constant temperature/humidity chamber.

After 5 hours exposure to the test humidity (without opening of chamber), the sample is removed and immediately covered tightly with a non-vapor permeable plastic film such as SARAN WRAP. After cooling about 30 minutes to allow for temperature equilibration, the plastic film is removed and the assembly is reweighed.

The MVTR value is then calculated by determining the moisture increase over 5 hours due to transport through the 3 cm circular opening and converting the result to units of grams per meter square per 24 hours (g/m²/24 hr). For each sample, three replicates should be run, the resulting values will be averaged, and the result rounded to the nearest 100 value.

F. Post-Compression Air Permeability

When a material, especially one with a relatively flexible or open structure, is subjected to compaction or sustained pressure, the material may experience structural changes. After the applied forces are removed, the material may not return to its original state completely. This residual structure change often results in changes in properties, such as air permeability. This test method is a measure of the resilience of the sample material after it has been subjected to compaction or a sustained pressure for a pre-determined period of time.

When an absorbent barrier structure of the present invention is incorporated into absorbent articles, such as diapers, the articles are often packaged in a highly compact condition, and stored under such condition for an extended period of time. Moreover, while the absorbent article is worn, the wearer may subject the article to sudden impact force (e.g., the wearer moves from a standing to a sitting position abruptly), which may be followed by a sustained pressure (e.g., the wearer maintains the sitting position). Certain materials or structures are susceptible to change under such conditions, and do not recover to their original state even after the compaction or pressure has been removed. Thus, a material or structure may have high air permeability when made, but may not be able to deliver such performance after it has been compacted and stored in a package or when it suffers sustained pressure applied by a wearer.

Samples (typically, multi-layered laminates) are cut to 40 mm by 165 mm in size. The samples are stacked and placed between two Plexiglas plates. Weight is applied over the Plexiglas plates, resulting in a pressure of 50 g/cm² (0.7 psi), thereby the overall caliper of the stack of sample sheets is reduced. The level of compression is calculated according to the following:

$$H = k \times n \times d$$

wherein

H is the overall caliper after pressure is applied to compress the sample stack;

d is the initial caliper of a sample sheet;

n is the number of sample sheets; and k is the compression level.

The compressed sample stacks are placed inside a climate-controlled chamber at 60° C., 50% relative humidity, for a pre-determined time period. Typically, the test is done with five samples in each stack and at 50% compression.

Air permeability of the sample is determined before compression and after 24 hours in compression. The post compression air permeability is measured after a waiting period, which is sufficient to allow the sample to recover (taking into consideration that the sample may exhibit permanent deformation and will not recover to its original, pre-compression state). For this test, the air permeability is determined by measuring the time in which a standard volume of air is drawn through the test specimen at a constant pressure and temperature.

The samples (e.g., the absorbent barrier structure prepared with pre- or post-compression sheets) are conditioned in a temperature and humidity controlled environment, at 22±2° C. and 35±15% relative humidity for at least 2 hours before testing.

The test equipment as manufactured by Hoppe & Schneider GmbH, Heidelberg, Germany, under the designation "Textiluhr nach Kretschmar", is essentially a bellows in a vertical arrangement, with its upper end being mounted in a fixed position, and the lower end being releasably held at its upper position, which can be loosened by means of a release handle to slide under controlled conditions to the lower position, thereby increasing the volume inside the bellows by pulling air through the test specimen which is covering the air entering opening at the upper end of the bellows. The test specimen is firmly held to cover the air entering opening by means of a fastening ring of 5 cm$^2$ or 10 cm$^2$ to allow for different samples sizes and/or different permeability ranges. If the 10 cm$^2$ ring is used, (he sample should be at least 55 mm wide, for the 5 cm$^2$ ring at least 35 mm. For both, the samples should have a length of about 150 mm.

In case of very high permeability materials, the opening can he further reduced, with appropriate adjustments to the equipment and calculation.

The equipment comprises a stopwatch ($\frac{1}{100}$ sec) which automatically measures the time between the operation of the release handle which starts the sliding of the bellows, and the stop of the bellows when their bottoms reach the lower end.

The air permeability k of the material is calculated by the Darcy law as described above, wherein different parameters are used (due to the differences in equipment set-up). Specifically for the test equipment used here, V is 1900 cm$^3$, A is 4.155 cm$^2$ and $\Delta p$ is 160 Pa.

The test is repeated once for each test sample (either sheets made of single material or laminates of different materials), and should be repeated on five samples. For each sample material or laminate, he average of at least three satisfactory runs is reported. The averaged value is reported in Darcy/mm, taking into account the unit thickness of the material.

G. Absorption Test

This test measures the high suction capillary absorption of absorbent materials. Capillary sorption is a fundamental property of any absorbent that governs how fluid would be absorbed by the absorbent structure. High suction capillary sorption characterizes the ability of a material to partition fluid from competing materials.

A porous glass frit is connected via an uninterrupted column of fluid to a fluid reservoir whose fluid level is located at the same height as the horizontal center of the frit porous structure. The sample absorbs fluid upon demand and its weight at equilibrium is recorded. The fixed height capsorption experiment thus gives information about the liquid uptake (g/g) in the horizontal direction.

Experimental Setup

The test liquid used herein is 0.2 wt % TRITON® X-100 (available from Sigma-Aldrich Inc.) aqueous solution having a surface tension of about 33 dyne/cm). This test method may be adapted to use other test liquids such as water or synthetic urine (having a surface tension of about 75 dyne/cm and about 55 dyne/cm. respectively).

A porous glass fritted funnel is filled with the test liquid. The fritted funnel (available from VWR Scientific Products, Cleveland, Ohio) has a 350 ml volume and 10.15 micron pores its bottom outlet is modified by glass blower to accommodate tubing. The fritted funnel is inverted such Chat the funnel opening is resting on a flat surface and the bottom outlet is facing up. A 1.40 in long piece of Tygon tubing (Part No. R3603, available from VWR Scientific Products) is attached to the funnel bottom and filled with test liquid. The fritted funnel is then turned uptight and clamped unto a stand. The Tygon Cubing end is secured to the fritted funnel with the tubing end raised several centimeters above the fritted disk.

The funnel is filled with 100 ml of test liquid (the raised tubing end prevents the liquid from draining through the frit) and covered with plastic wrap. The frit is then stored for 5–12 hours to allow any air trapped in the frit pores to escape. Any observable air bubbles should also be removed from the frit or the tubing. For testing, the Tygon tubing is placed in the glass fluid reservoir (20–25 cm diameter) filled with test liquid. The center of the frit and the fluid level in the reservoir are set to the same height. A level is used to ensure that the frit surface is horizontal. In between experiments the fritted funnel is covered with plastic wrap to prevent evaporation and drying of the test liquid in the frit pores; however, during an experiment the fritted funnel is not covered. If frits are not used for several hours, they should be stored as follows: the Tygon tubing is removed from the fluid reservoir and secured to the fritted funnel with the tubing end raised several centimeters above the fritted disk. The funnel is filled with 100 ml of test liquid (the raised tubing end prevents the liquid from draining through the frit) and covered with plastic wrap.

Experimental Procedure

Ensure that no observable air bubbles are trapped below the frit or in the tubing. Cut a 5.40 cm diameter sample using an arch punch. Weigh the sample. Clamp off tubing below fritted funnel. Place the pup cylinder onto the frit surface centered. Place the sample into the pup cylinder, making sure that it is centered and lying flat on the frit surface. Gently insert the pup piston into the pup cylinder over the sample. Place a ring weight on the pup cylinder. Remove the clamp and allow the samples to absorb for 2.5 minutes. Remove the ring weight, the pup piston, the pup cylinder and then the sample from frit. If it is necessary to lower the fritted funnel or tilt it for sample removal, the fritted funnel tubing has to be clamped off below the fritted funnel prior to removing the sample from the frit (to ensure that no additional fluid is absorbed by the sample during removal). Weigh the sample. Repeat procedure with the next sample. Perform two replicates for each sample and report the net uptake obtained for each sample as well as the average net uptake. Report which frits were used (frit number or other identification). If results of the two tests differ by more than 10% (based on the higher value), check frits and sample preparation and repeat the experiment. The liquid absorption (or uptake) by the sample is calculated according to the following: Net uptake, g/g=(sample wet weight, g–sample dry weight, g)/sample dry weight, g

EXAMPLES

Example 1

In this example, the absorbent barrier structure of the present invention is a two-layered laminate comprising an absorbent zone and a barrier zone substantially superimposed over the barrier zone. FIG. 2A illustrates this embodiment schematically, wherein the absorbent barrier structure 10 includes a barrier layer 12 and an absorbent layer 14. The absorbent layer is a natural fiber cellulosic web commercially available as BOUNTY® paper towel (manufactured by the Procter and Gamble Company, Cincinnati, Ohio). BOUNTY® has a two-ply construction, with a total basis weight of about 43 gsm and a total thickness of about 0.686 mm. The barrier layer is a polypropylene spunbond/meltblown nonwoven web (manufactured by BBA Nonwovens, Simpsonville, S.C. under the designation MD2005) which has a basis weight of about 27 gsm and a thickness of about 0.305 mm.

Example 2

In this example, the absorbent barrier structure has a three-layered structure, which includes a first and a second barrier zones are disposed on the opposed sides of the absorbent zone. FIG. 2B illustrates this embodiment schematically, wherein the absorbent barrier structure 10 includes two barrier layers 12 and 16 and an absorbent layer 14 between the two barrier layers. The absorbent layer is a two-ply BOUNTY® paper towel. The first and the second barrier layers are meltblown polypropylene nonwoven webs (manufactured by Jentex Corporation, Buford, Ga. with the designation PP-015-F-N, X2009A). Each of the MB nonwoven web has a basis weight of about 15 gsm.

Example 3

In this example, the absorbent barrier structure has substantially the same construction as described in Example 2, except that the first barrier layer is a MB polypropylene nonwoven web from Jentex (PP-010-F-N, X2009A) with a basis weight of about 10 gsm. The second barrier layer is a spunbond/spunbond polypropylene nonwoven web made of microdenier fibers with a basis weight of about 17 gsm (available from First Quality Fibers Nonwovens, Hazelton, Pa. under the designation GCAS 16002184).

Example 4

In this example, the absorbent barrier structure has substantially the same construction as described in Example 2, except that the first barrier layer is a MB nonwoven web from Jentex (PP-005-F-N, X2009A) with a basis weight of about 5 gsm and the second barrier layer is a MB nonwoven web from Jentex (PP-010-F-N, X2009A) with a basis weight of about 10 gsm.

Example 5

In this example, the absorbent barrier structure has substantially the same construction as described in Example 2, except that the first barrier layer is a MB nonwoven web from Jentex (PP-010-F-N, X2009A) with a basis weight of about 10 gsm and the second barrier layer is a MB nonwoven web from Jentex (PP-005-F-N, X2009A) with a basis weight of about 5 gsm.

Example 6

In this example, the absorbent barrier structure has substantially the same construction as described in Example 2, except that the absorbent layer is a single-ply BOUNTY® paper towel.

Example 7

In this example, the absorbent barrier structure has substantially the same construction as described in Example 3, except that the absorbent layer is a single-ply BOUNTY® paper towel.

Example 8

In this example, the absorbent barrier structure has substantially the same construction as described in Example 2, except that the absorbent layer comprises two superimposed layers of single-ply BOUNTY® paper towel.

The properties of the above examples are tested according to the Test Methods disclosed herein. For the three-layered structure, the first barrier layer is disposed adjacent to the absorbent core during the tests. The results are summarized in Table 1 below. The test results in Table 1 indicate that the present invention provides a unique structure having the desirable balance of properties.

TABLE 1

| EXAMPLE | AIR PERMEABILITY (Darcy/mm) | HYDROHEAD PRESSURE (mBars) | LIQUID IMPACT TRANSMISSION VALUE (gsm) | BASIS WEIGHT (gsm) |
| --- | --- | --- | --- | --- |
| 1 | 57 | 41.3 | 7.2 | 70 |
| 2 | 24 | 49.3 | 6.8 | 73 |
| 3 | 51 | 45.3 | 8.3 | 69.3 |
| 4 | 47 | 23.5 | 7.4 | 57.1 |
| 5 | 46 | 39.3 | 8.5 | 57.1 |
| 6 | 24 | 55.5 | 10.5 | 54 |
| 7 | 59 | 33.7 | 13.2 | 51 |
| 8 | 21.4 | 81.5 | 7.1 | 78 |

Comparative Examples

Comparative Example 1 is a two-ply BOUNTY® paper towel.

Comparative example 2 is a formed film having angled capillaries on its surface such as those described in EP 934,735 and EP 934,736. The formed film is made of polyethylene and is available from Tredegar Film Products Corporation, Terre Haute, Ind.

Comparative example 3 is a microporous film. The microporous film is made of polyethylene having 40–45 wt % CaCO3 fillers. The microporous film is available from Clopay Plastic Products Company, Cincinnati, Ohio.

Comparative example 4 is a polypropylene SS nonwoven web available from First Quality Fibers Nonwovens, Hazelton, Pa. under the designation GCAS 16002184.

Comparative Example 5 is a polypropylene MB nonwoven web available from Jentex Corporation, Buford, Ga.) with the designation PP-015-F-N, X2009A.

The properties of the comparative examples are tested according to the Test Methods disclosed herein. For the three-layered structure, the first barrier layer is disposed adjacent to the absorbent core during the test results are summarized in Table 2 below.

TABLE 2

| COMPARATIVE EXAMPLE | AIR PERMEABILITY (Darcy/mm) | HYDROHEAD PRESSURE (mBars) | LIQUID IMPACT TRANSMISSION VALUE (gsm) | BASIS WEIGHT (gsm) |
|---|---|---|---|---|
| 1 | 143 | <0.5 | 57 | 43 |
| 2 | 133 | 3 | 5 | 42 |
| 3 | 0.05 | >100 | 0.2 | 52 |
| 4 | 407 | 10.8 | 37 | 17 |
| 5 | 53 | 68.5 | 25 | 15 |

The test results in Table 2 indicate that the comparative examples fail to provide the desirable balance of properties. BOUNTY® paper towel (Comparative example 1) has excellent air permeability but poor liquid impermeability. Microporous film (Comparative example 2) has excellent liquid impermeability but is substantially air impermeable. The nonwoven webs (Comparative examples 3–5) are air permeable and liquid impermeable under general conditions. However, the nonwoven webs become liquid permeable under impact and/or pressure conditions.

Example 9

In this example, the absorbent barrier structure has a three-layered construction as described in Example 2 is combined with an outer cover material, which is a polypropylene SM nonwoven web having a 16 gsm SB layer and a 11.5 gsm MB layer. The combination structure is tested according to the Test Methods described herein. The test results are summarized in Table 3.

TABLE 3

| EXAMPLE | AIR PERMEABILITY (Darcy/mm) | HYDROHEAD PRESSURE (mBars) | LIQUID IMPACT TRANSMISSION VALUE (gsm) |
|---|---|---|---|
| 9 | 13 | 71.7 | 5.1 |
| 2 | 24 | 49.3 | 6.8 |

When compared to the absorbent barrier structure of Example 2, the combined structure enhances the liquid impermeability and resistance to wet-through under impact but decreases the air permeability. Overall, the combined structure also provides the desired balance of properties.

Example 10

In this example, the absorbent barrier structure of Example 2 is combined with an outer cover material according to Example 9. Further, an apertured film is disposed between the second barrier layer of Example 2 and the outer cover of Example 9. The apertured film is made of polyethylene having 11.7% open area. The apertures are hexagonal-shaped openings. The apertured film used herein is manufactured by BP Chemicals, Wassergurg, Germany under the trade designation (HEX-B Type. 45109). Apertured films manufactured by Tredegar Film Products Corporation, Terre Haute, Ind., under the designation HEX-B, are equally suitable for use herein.

The overall structure, including the absorbent barrier structure, the apertured film and the outer cover, are tested according to the Test Methods described herein, and are compare with Example 9, which does not include the apertured film. The results are summarized in Table 4 below.

TABLE 4

| EXAMPLE | AIR PERMEABILITY (Darcy/mm) | HYDROHEAD PRESSURE (mBars) | LIQUID IMPACT TRANSMISSION VALUE (gsm) | MVTR (g/m$^2$/24 hrs) |
|---|---|---|---|---|
| 9 | 13 | 71.7 | 5.1 | 3972 |
| 10 | 13 | 66.2 (±10) | 2.5 | 3434 |

The open structure of the apertured film has insubstantial effect on the convective air permeability overall. The apertured film reduces the liquid impermeability of the overall structure, especially under impact condition. The results show that the overall structure including the addition of the apertured film, still achieves the desired balance of properties. More importantly, the apertured film reduces the diffusive MVTR of the overall structure. Thus, the unique combination of permeabilities provides a structure that desirably exhibits reduced dampness or condensation on the outer surface of the structure.

Example 11

In this example, the absorbent layer is a cellulosic web (namely, a two-ply BOUNTY® towel) which has been surface-treated with a hydrophobic agent on both sides. The surface treatment method is described in PCT publication WO 00/14296 (D'Agostino et al.) (corresponding to U.S. Ser. No. 09/786,075), the disclosure of which is incorporated herein by reference. The hydrophobic agent used is a fluorocarbon, namely, perfluoromethylcyclohexane. The treated cellulosic web is disposed between two barrier layers to form a three-layered absorbent barrier structure. Example 11 has substantially the same structure as Example 2 except that the treated BOUNTY® is used in place of the untreated BOUNTY® as the absorbent layer. Table 5 below shows the properties of this example in comparison to the example using the untreated web.

TABLE 5

| EXAMPLE | AIR PERMEABILITY (Darcy/mm) | HYDROHEAD PRESSURE (mBars) | LIQUID IMPACT TRANSMISSION VALUE (gsm) |
|---|---|---|---|
| 11 | 27 | 74.3 | 4.7 |
| 2 | 24 | 49.3 | 6.8 |

The results show that the hydrophobic treatment significantly enhances the liquid impermeability while maintaining the air permeability.

Example 12

In this example, example 12 and Comparative example 2 are tested according to Test Method G (Post-Compaction Air Permeability). Example 12 has substantially the same construction as example 3, except that both the first and the second barrier layers are spunbond/spunbond polypropylene nonwoven webs made of microdenier fibers with a basis weight of about 17 gsm (available from First Quality Fibers Nonwovens, Hazelton, Pa. under the designation GCAS 16002184). The results are summarized below in Table 6.

TABLE 6

| EXAMPLE | PRE-COMPACTION AIR PERMEABILITY (Darcy/mm) | POST-COMPACTION AIR PERMEABILITY (Darcy/mm) |
|---|---|---|
| Comp. 2 | 109 ± 10 | 66 ± 16 |
| 12 | 115 ± 7 | 94 ± 8 |

As the test results show that compaction results in insubstantial change in air permeability of example 12 of the absorbent barrier structure of the present invention. In contrast, a material, such as Comparative example 2, suffers significant loss in air permeability, which is attributable to its structural changes under compaction and its inability to recover its original structure.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a topsheet;
   b. an outer cover;
   c. an absorbent core disposed between the topsheet and the outer cover;
   d. an absorbent barrier structure is disposed between the absorbent core and the outer cover wherein the absorbent barrier structure has a hydrohead value of at least about 10 mBars: a convective air permeability of at least about 10 Darcy/mm; and a liquid impact transmission value of less than about 20 g/m² and wherein said absorbent barrier structure is substantially free of a film; and wherein said barrier structure comprises:
      1) a first barrier zone disposed adjacent to a garment-facing surface of the absorbent core and a reservoir zone disposed between the barrier zone and the outer cover;
      2) a second barrier zone disposed at least partially between the reservoir zone and the outer cover
      3) a dampness management means disposed between the absorbent barrier structure and the outer cover, or between the reservoir zone and one of the barrier zones
   wherein a combination of the absorbent barrier structure and the outer cover has a hydrohead value of at least about 25 mBars: a convective air permeability of at least about 10 Darcy/mm; and a liquid impact transmission value of less than about 20 g/m².

2. The absorbent structure of claim 1 wherein the absorbent barrier structure, the dampness management means and the outer cover together has a MVTR of no more than 4500 g/m²/24 hrs.

3. The absorbent structure of claim 1 wherein the dampness management means is an apertured film having no more than about 20% open surface area.

4. An absorbent article comprising:
   a. a topsheet;
   b. an outer cover that is a nonwoven web or apertured film;
   c. an absorbent core disposed between the topsheet and the outer cover; and
   d. an absorbent barrier structure that is substantially free of a film is disposed between the absorbent core and the outer cover and comprising:
      1) a first fibrous barrier zone that is a nonwoven web and is disposed adjacent to a garment-facing surface of the absorbent core;
      2) a reservoir zone that is a cellulosic web and is disposed between the first fibrous barrier zone and the outer cover;
      3) a second fibrous barrier zone disposed between the reservoir zone and the outer cover; and
   wherein the barrier structure has
      a convective air permeability of greater than about 10 Darcy/mm;
      a liquid impact transmission value of less than about 20 g/m²; and
      a post-compression air permeability decrease of no more than about 35%; and
   wherein the combination of the absorbent barrier structure and the outer cover has
      a hydrohead value of at least about 10 mBars;
      a convective air permeability of at least about 10 Darcy/mm; and
      a liquid impact transmission value of less than about 20.

5. The absorbent article of claim 4 further comprising a dampness management means disposed between the barrier structure and the outer cover or between the reservoir zone and one of the barrier zones.

6. The absorbent article of claim 5 wherein the dampness management means is an apertured film having less than about 20% open surface area.

* * * * *

UNITED STATES PATENT AND TRADEMARK OFFICE
CERTIFICATE OF CORRECTION

PATENT NO. : 7,179,951 B2
APPLICATION NO. : 10/265813
DATED : February 20, 2007
INVENTOR(S) : Srinivas Krishnaswamy-Mirle et al.

It is certified that error appears in the above-identified patent and that said Letters Patent is hereby corrected as shown below:

Column 8
Line 53, delete "µg" and insert -- g/g --.
Column 16
Line 2, delete "Chananooga" and insert -- Chattanooga --.
Column 29
Line 19, delete "(he" and insert -- the --.
Line 24, delete "he" and insert -- be --.
Line 39, delete "he" and insert -- the --.
Line 64, delete "dyne/cm." and insert -- dyne/cm, --.
Line 67, delete "10.15" and insert -- 10-15 --.
Column 30
Line 1, insert -- ; -- after "pores".
Line 3, delete "Chat" and insert -- that --.
Line 4, delete "in" and insert -- m --.
Line 7, delete "uptight" and insert -- upright --.
Line 8, delete "unto" and insert -- onto --.
Line 8, delete "Cubing" and insert -- tubing --.
Column 32
Line 19, delete "The results" and insert -- The test results --.
Line 66, delete "during the" and insert -- during the tests. The --.
Column 35
Line 33, delete ":" and insert -- ; --.
Line 50, delete ":" and insert -- ; --.
Column 36
Line 41, delete "20." and insert --20 $g/m^2$. --.

Signed and Sealed this

Seventh Day of August, 2007

JON W. DUDAS
*Director of the United States Patent and Trademark Office*